US006806053B1

(12) United States Patent
Sportsman et al.

(10) Patent No.: US 6,806,053 B1
(45) Date of Patent: Oct. 19, 2004

(54) CELL-SIGNALING ASSAYS

(75) Inventors: J. Richard Sportsman, Palo Alto, CA (US); Lawrence M. Kauvar, San Francisco, CA (US)

(73) Assignee: LJL BioSystems, Inc., Sunnyvale, CA (US)

( * ) Notice: Subject to any disclaimer, the term of this patent is extended or adjusted under 35 U.S.C. 154(b) by 0 days.

(21) Appl. No.: 09/768,661

(22) Filed: Jan. 23, 2001

Related U.S. Application Data

(63) Continuation of application No. PCT/US00/16012, filed on Jun. 9, 2000.
(60) Provisional application No. 60/200,594, filed on Apr. 28, 2000, provisional application No. 60/182,036, filed on Feb. 11, 2000, and provisional application No. 60/138,311, filed on Jun. 9, 1999.

(51) Int. Cl.[7] .................. G01N 33/533; G01N 33/53; C12P 21/00
(52) U.S. Cl. .................. 435/7.1; 435/70.21; 436/518
(58) Field of Search ................. 435/7.1, 70.21; 436/518; 530/334, 300, 350

(56) References Cited

U.S. PATENT DOCUMENTS 5,225,543 A   7/1993   Eppler et al.

FOREIGN PATENT DOCUMENTS

| WO | WO98/0562 | 2/1998 |
| WO | WO00/75332 | 12/2000 |

OTHER PUBLICATIONS

Allen et al. (Feb. 2002) "A Homogeneous High Throughput Nonradioactive Method for Measurement of Functional Activity of Gs–Coupled Receptors in Membranes." Journal of Biomolecular Screening 7(1): 35–44.*

Huang et al. (Jun. 2002) "A Fluorescence Polarization Assay for Cyclic Nucleotide Phosphodiesterases." Journal of Biomolecular Screening 7(3): 215–222.*

Prystay et al. (Apr. 2002) "Homogenous Cell–Based Fluorescence Polarization Assay for the Direct Detection of cAMP." Journal of Biomolecular Screening 6(2): 75–82.*

A Biolumnescent Assay for Agonist Activity at Potentially Any G–Protein–Coupled Receptor, Stables et al., *Analytical Biochemistry*, 252: 115–126 (1997).

Monoclonal Antibodies as Sarrogate Receptors in a High Throughput Screen for Compounds that Enhance Insulin Sensitivity, Bright et al., *Life Science*, vol. 61, No. 23, pp. 2305–2315 (1997).

Random Insertion of GFP into cAMP Dependent Protein Kinase Regulatory Subunit From *Dictyostelium Discoideum*, Biondi et al., *Nucleic Acids Research*, vol. 26, No. 21, pp. 4946–4952.

* cited by examiner

*Primary Examiner*—Brenda Brumback
*Assistant Examiner*—Christopher James Nichols
(74) *Attorney, Agent, or Firm*—Kolisch Hartwell, P.C.

(57) ABSTRACT

Assays for detecting the presence and activity of cell-signaling components. These assays include luminescence polarization assays for detecting cell-signaling nucleotides and modulators of receptors and enzymes related to the generation and activity of such nucleotides.

25 Claims, 11 Drawing Sheets

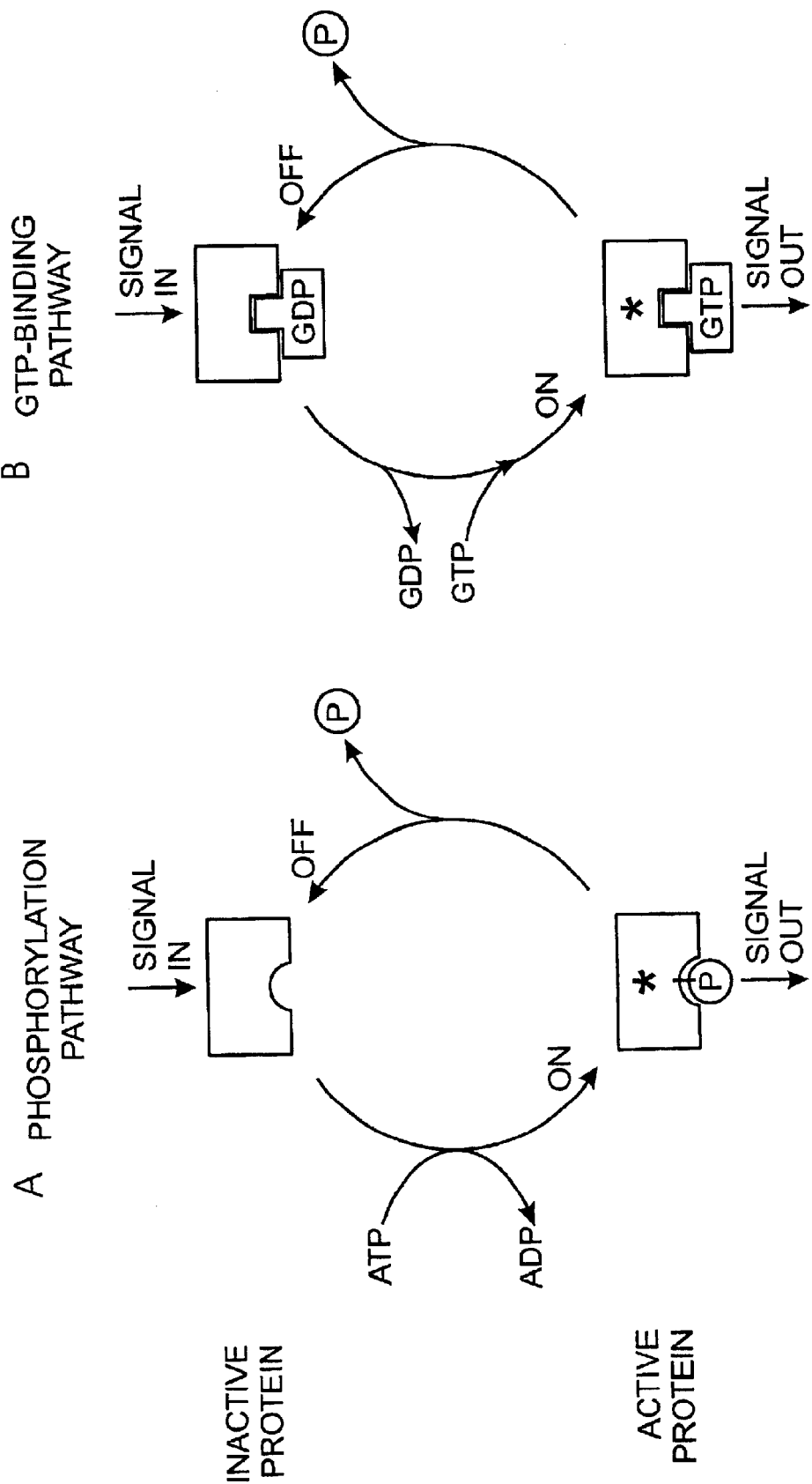

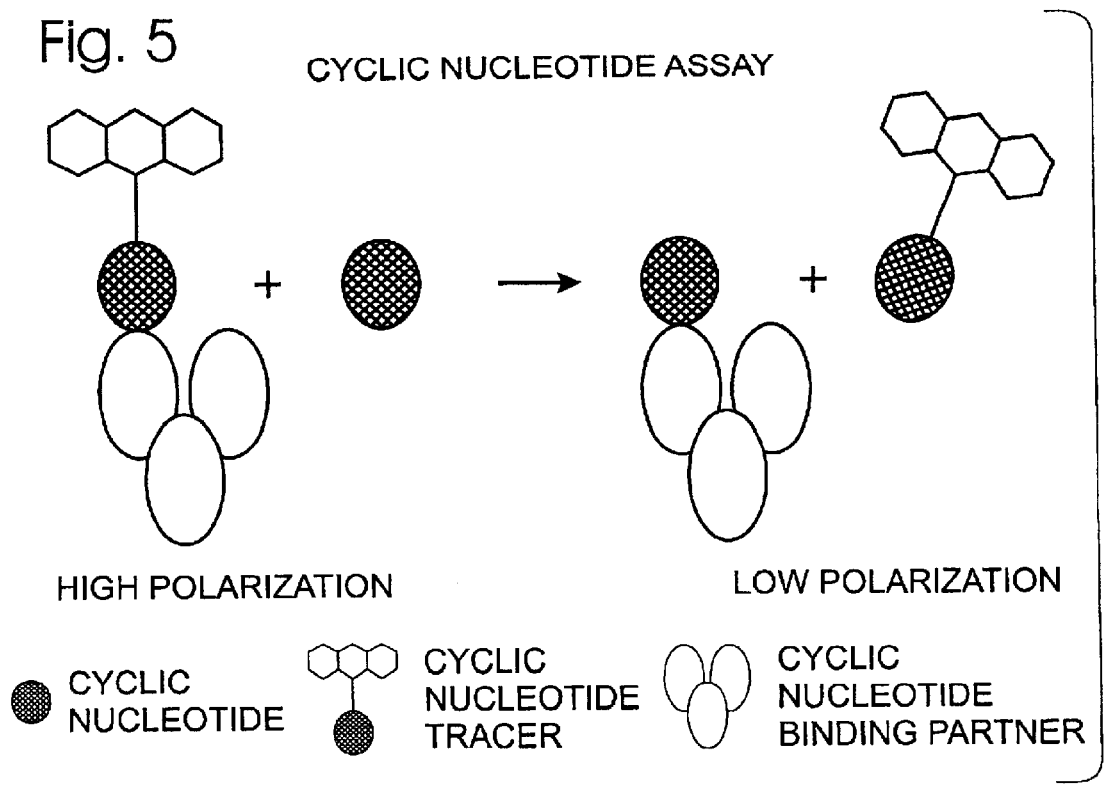
Fig. 5 CYCLIC NUCLEOTIDE ASSAY
HIGH POLARIZATION          LOW POLARIZATION
● CYCLIC NUCLEOTIDE    CYCLIC NUCLEOTIDE TRACER    CYCLIC NUCLEOTIDE BINDING PARTNER
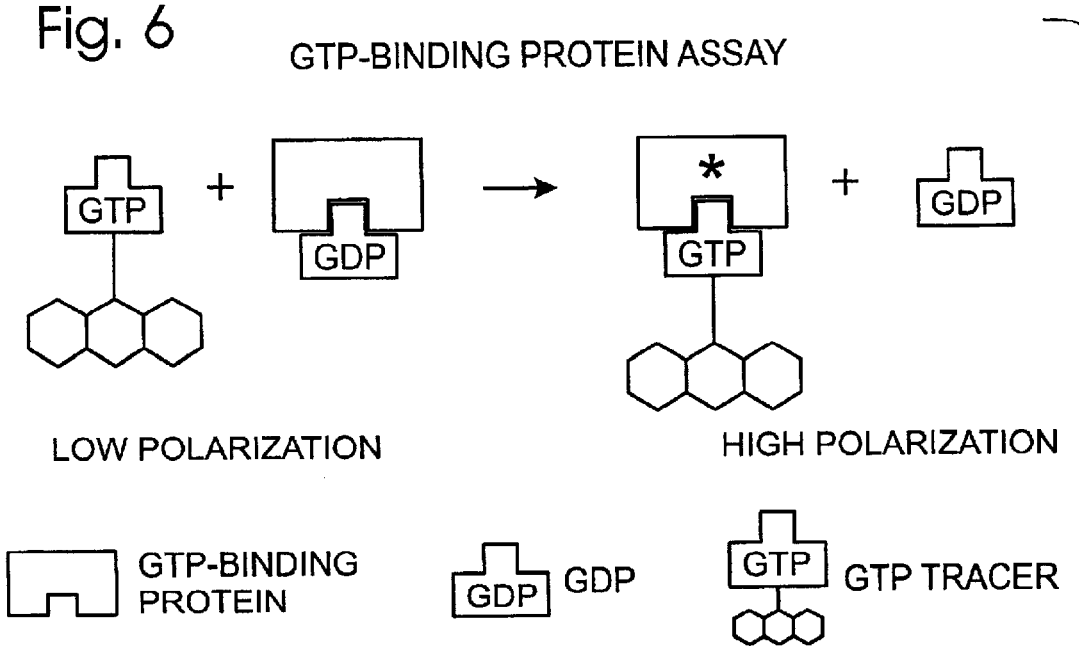
Fig. 6 GTP-BINDING PROTEIN ASSAY
LOW POLARIZATION          HIGH POLARIZATION
GTP-BINDING PROTEIN    GDP    GTP TRACER Fig. 7A
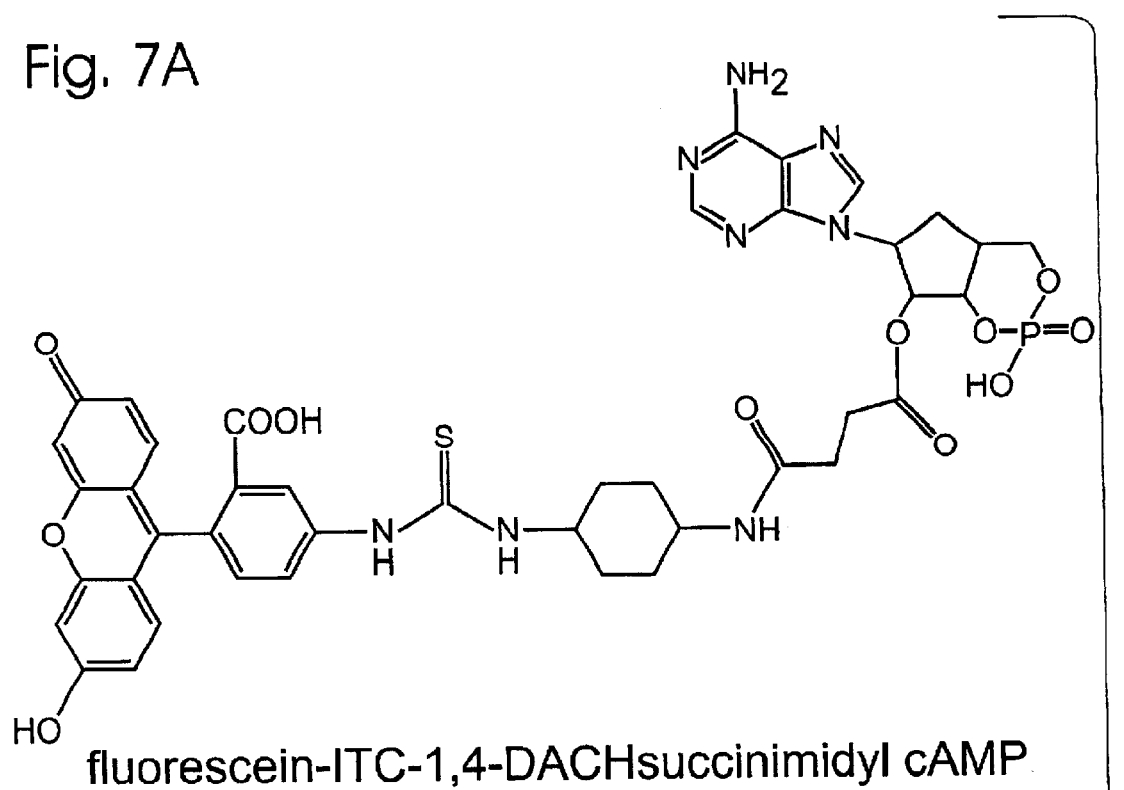
fluorescein-ITC-1,4-DACHsuccinimidyl cAMP
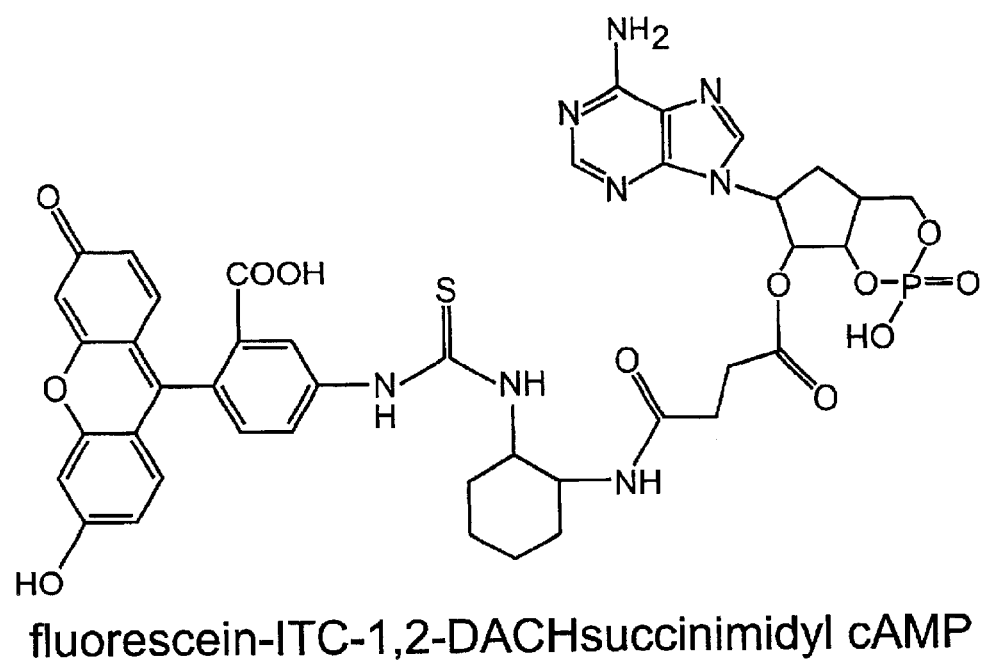
fluorescein-ITC-1,2-DACHsuccinimidyl cAMP Fig. 7B
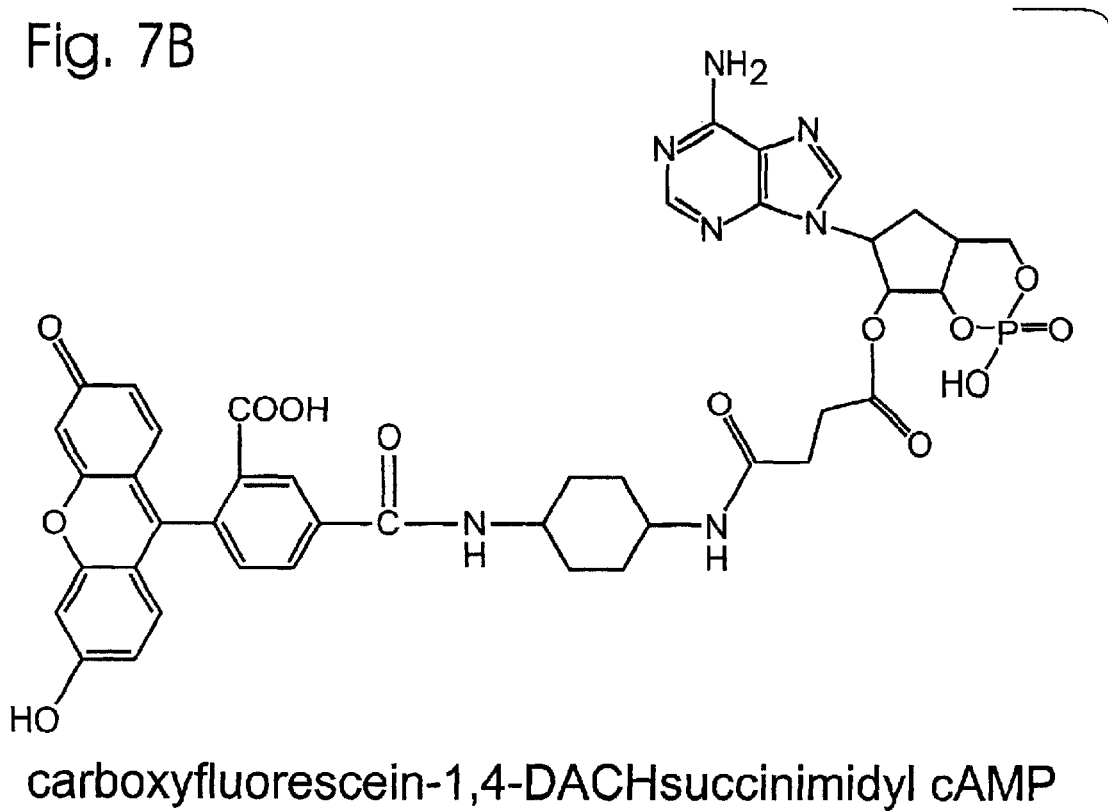
carboxyfluorescein-1,4-DACHsuccinimidyl cAMP
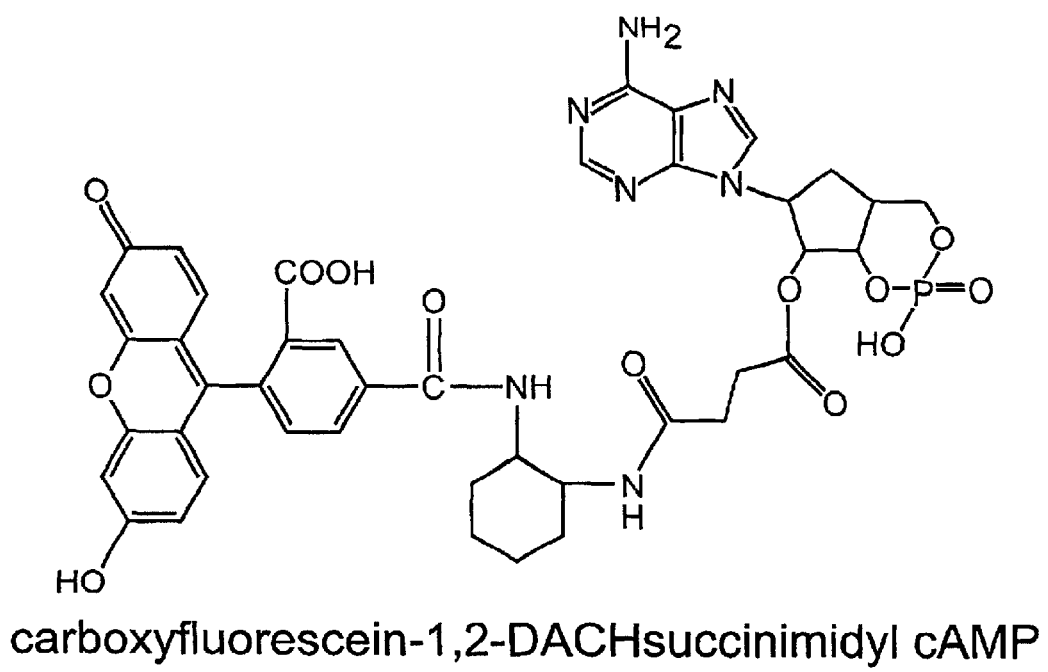
carboxyfluorescein-1,2-DACHsuccinimidyl cAMP Fig. 8A
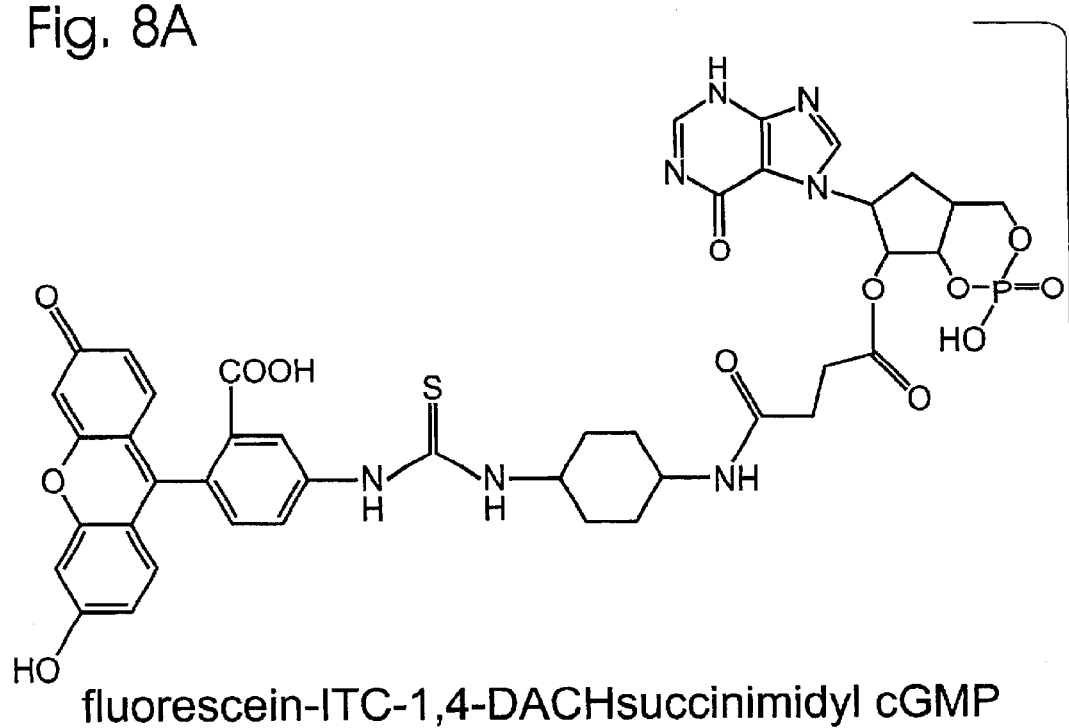
fluorescein-ITC-1,4-DACHsuccinimidyl cGMP
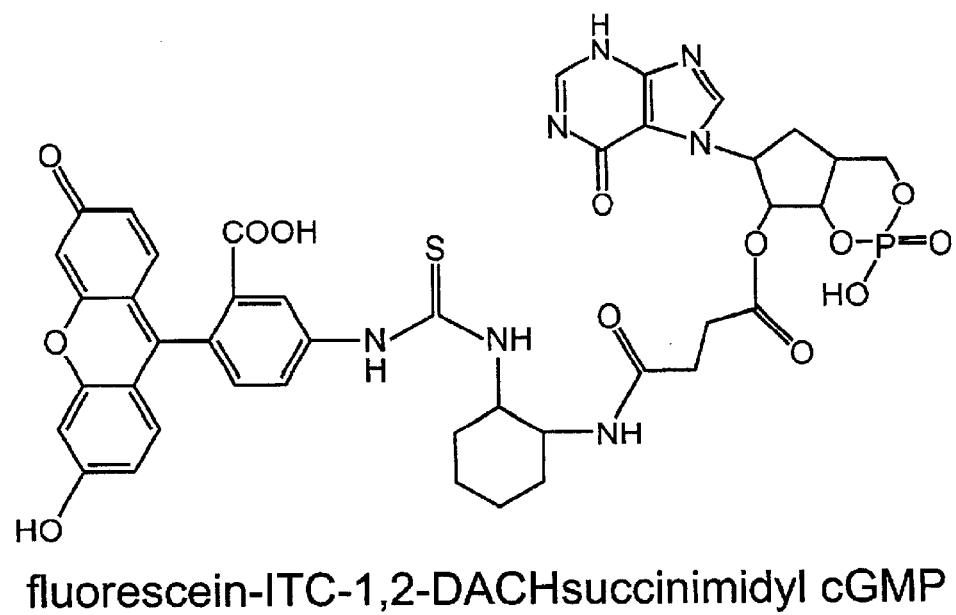
fluorescein-ITC-1,2-DACHsuccinimidyl cGMP Fig. 8B
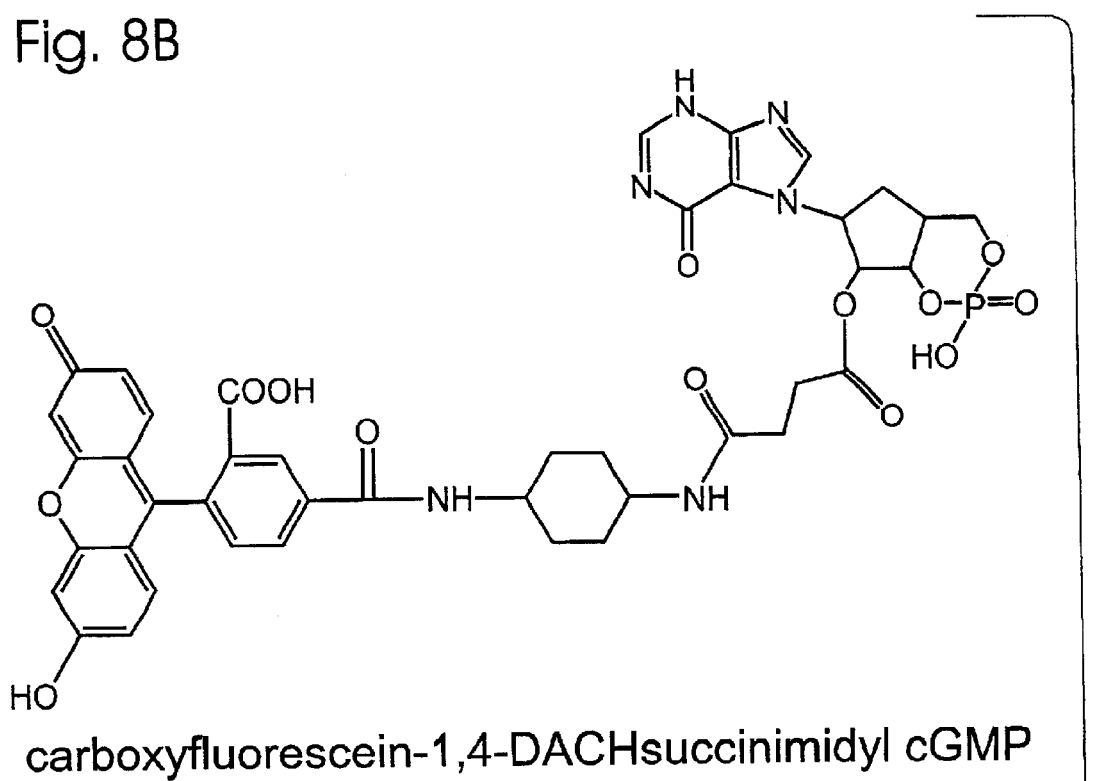
carboxyfluorescein-1,4-DACHsuccinimidyl cGMP
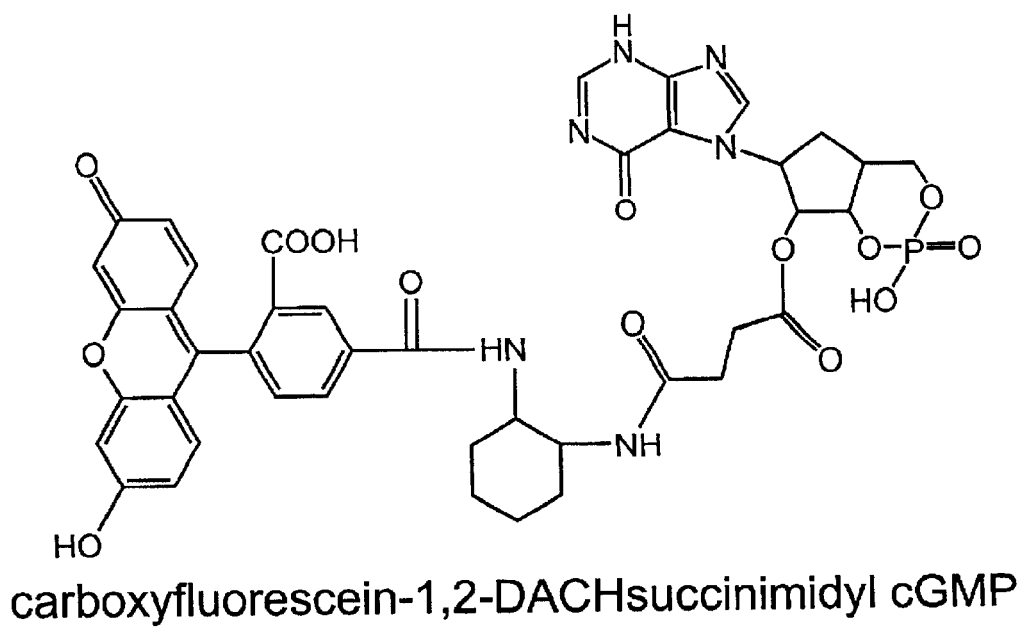
carboxyfluorescein-1,2-DACHsuccinimidyl cGMP

Fig. 9A

| | 1 [cAMP CALIBRATORS] | 2 [CONTROLS] | 3 [SAMPLES] |
|---|---|---|---|
| A | 10 μL BUFFER<br>10 μL cAMP Ab WORKING STOCK<br>10 μL 10 μM CALIBRATOR<br>10 μL cAMP TRACER WORKING STOCK | 40 μL BUFFER | 10 μL BUFFER<br>10 μL cAMP Ab WORKING STOCK<br>10 μL SAMPLE 1<br>10 μL cAMP TRACER WORKING STOCK |
| B | → | → | → |
| C | 10 μL BUFFER<br>10 μL cAMP Ab WORKING STOCK<br>10 μL 3.33 μM CALIBRATOR<br>10 μL cAMP TRACER WORKING STOCK | → | 10 μL BUFFER<br>10 μL cAMP Ab WORKING STOCK<br>10 μL SAMPLE 2<br>10 μL cAMP TRACER WORKING STOCK |
| D | → | → | → |
| E | 10 μL BUFFER<br>10 μL cAMP Ab WORKING STOCK<br>10 μL 1.11 μM CALIBRATOR<br>10 μL cAMP TRACER WORKING STOCK | 30 μL BUFFER<br>10 μL cAMP Ab WORKING STOCK | 10 μL BUFFER<br>10 μL cAMP Ab WORKING STOCK<br>10 μL SAMPLE 3<br>10 μL cAMP TRACER WORKING STOCK |
| F | → | → | → |
| G | 10 μL BUFFER<br>10 μL cAMP Ab WORKING STOCK<br>10 μL 0.37 μM CALIBRATOR<br>10 μL cAMP TRACER WORKING STOCK | → | 10 μL BUFFER<br>10 μL cAMP Ab WORKING STOCK<br>10 μL SAMPLE 4<br>10 μL cAMP TRACER WORKING STOCK |
| H | → | → | → |

Fig. 9B

| | 1 [cAMP CALIBRATORS] | 2 [CONTROLS] | 3 [SAMPLES] |
|---|---|---|---|
| I | 10 μL BUFFER<br>10 μL cAMP Ab WORKING STOCK<br>10 μL 0.12 μM CALIBRATOR<br>10 μL cAMP TRACER WORKING STOCK | 30 μL BUFFER<br>10 μL TRACER WORKING STOCK | 10 μL BUFFER<br>10 μL cAMP Ab WORKING STOCK<br>10 μL SAMPLE 5<br>10 μL cAMP TRACER WORKING STOCK |
| J | → | → | → |
| K | 10 μL BUFFER<br>10 μL cAMP Ab WORKING STOCK<br>10 μL 0.041 μM CALIBRATOR<br>10 μL cAMP TRACER WORKING STOCK | → | 10 μL BUFFER<br>10 μL cAMP Ab WORKING STOCK<br>10 μL SAMPLE 6<br>10 μL cAMP TRACER WORKING STOCK |
| L | → | → | → |
| M | 10 μL BUFFER<br>10 μL cAMP Ab WORKING STOCK<br>10 μL 0.014 μM CALIBRATOR<br>10 μL cAMP TRACER WORKING STOCK | 20 μL BUFFER<br>10 μL cAMP Ab WORKING STOCK<br>10 μL cAMP TRACER WORKING STOCK | 10 μL BUFFER<br>10 μL cAMP Ab WORKING STOCK<br>10 μL SAMPLE 7<br>10 μL cAMP TRACER WORKING STOCK |
| N | → | → | → |
| O | 10 μL BUFFER<br>10 μL cAMP Ab WORKING STOCK<br>10 μL 0.005 μM CALIBRATOR<br>10 μL cAMP TRACER WORKING STOCK | → | 10 μL BUFFER<br>10 μL cAMP Ab WORKING STOCK<br>10 μL SAMPLE 8<br>10 μL cAMP TRACER WORKING STOCK |
| P | → | → | → |

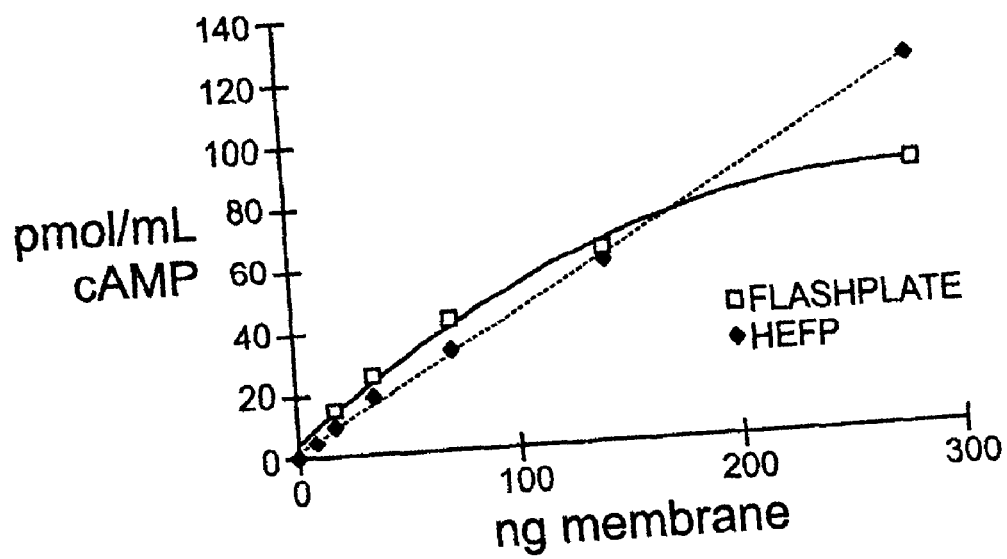
Fig. 12 Purified Adenylate Cyclase
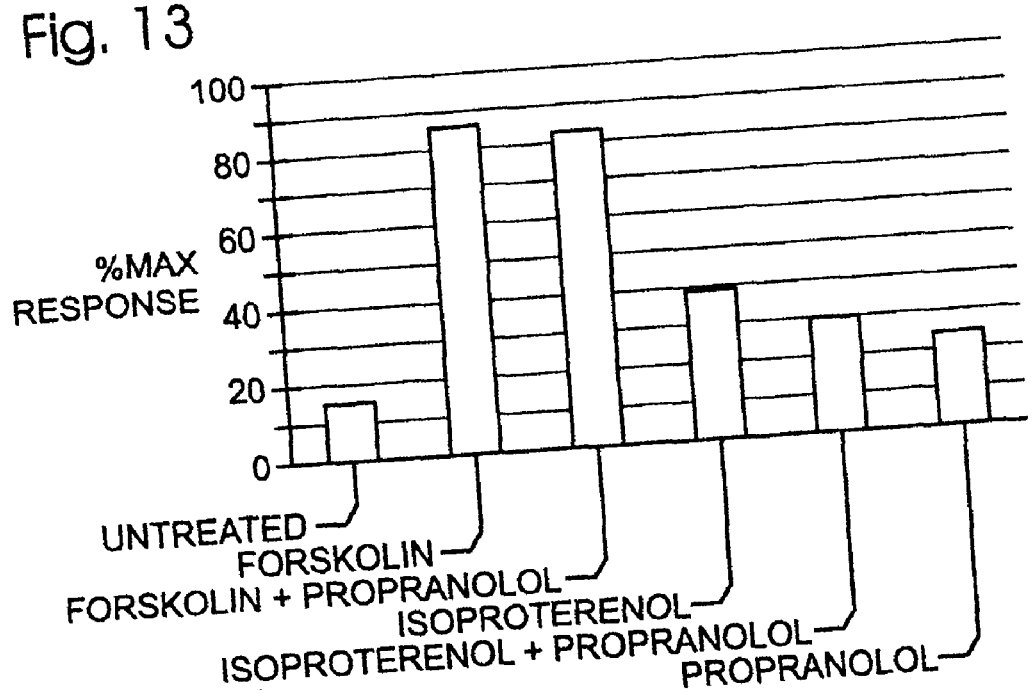
Fig. 13

CELL-SIGNALING ASSAYS

CROSS-REFERENCES

This application is a continuation of PCT Patent Application Serial No. PCT/US00/16012, filed Jun. 9, 2000, which is incorporated herein by reference.

This application is based upon and claims priority under 35 U.S.C. §119 from the following U.S. Provisional Patent Applications, each of which is incorporated herein by reference: Ser. No. 60/138,311, filed Jun. 9, 1999; Ser. No. 60/182,036, filed Feb. 11, 2000; and Ser. No. 60/200,594, filed Apr. 28, 2000.

This application incorporates by reference the following U.S. patent applications: Ser. No. 08/840,553, filed Apr. 14, 1997; Ser. No. 08/929,095, filed Sep. 15, 1997; Ser. No. 09/118,141, filed Jul. 16, 1998; Ser. No. 09/144,575, filed Aug. 31, 1998; Ser. No. 09/144,578, filed Aug. 31, 1998; Ser. No. 09/146,081, filed Sep. 2, 1998; Ser. No. 09/156,318, filed Sep. 18, 1998; Ser. No. 09/160,533, filed Sep. 24, 1998; Ser. No. 09/302,159, filed Apr. 29, 1999; Ser. No. 09/349,733, filed Jul. 8, 1999; Ser. No. 09/468,440, filed Dec. 21, 1999; Ser. No. 09/478,819, filed Jan. 5, 2000; Ser. No. 09/494,407, filed Jan. 28, 2000; and Ser. No. 09/556,030, filed Apr. 20, 2000.

This application also incorporates by reference the following PCT patent applications: Serial No. PCT/US99/01656, filed Jan. 25, 1999; Serial No. PCT/US99/03678, filed Feb. 19, 1999; Serial No. PCT/US99/08410, filed Apr. 16, 1999; Serial No. PCT/US99/16057, filed Jul. 15, 1999; Serial No. PCT/US99/16453, filed Jul. 21, 1999; Serial No. PCT/US99/16621, filed Jul. 23, 1999; Serial No. PCT/US99/16286, filed Jul. 26, 1999; Serial No. PCT/US99/16287, filed Jul. 26, 1999; Serial No. PCT/US99/24707, filed Oct. 19, 1999; Serial No. PCT/US00/00895, filed Jan. 14, 2000; Serial No. PCT/US00/03589, filed Feb. 11, 2000; Serial No. PCT/US00/04543, filed Feb. 22, 2000; Serial No. PCT/US00/06841, filed Mar. 15, 2000; Serial No. PCT/US00/12277, filed May 3, 2000; Serial No. PCT/US00/16025, filed Jun. 9, 2000; and Serial No. PCT/US00/15774, filed Jun. 9, 2000.

This application also incorporates by reference the following U.S. provisional patent applications: Ser. No. 60/138,438, filed Jun. 10, 1999; Ser. No. 60/138,737, filed Jun. 11, 1999; Ser. No. 60/138,893, filed Jun. 11, 1999; Ser. No. 60/142,721, filed Jul. 7, 1999; Ser. No. 60/143,185, filed Jul. 9, 1999; Ser. No. 60/153,251, filed Sep. 10, 1999; Ser. No. 60/164,633, filed Nov. 10, 1999; 60/165,813, filed Nov. 16, 1999; Ser. No. 60/167,301, filed Nov. 24, 1999; Ser. No. 60/167,463, filed Nov. 24, 1999; Ser. No. 60/178,026, filed Jan. 26, 2000; Ser. No. 60/182,419, filed Feb. 14, 2000; Ser. No. 60/184,719, filed Feb. 24, 2000; Ser. No. 60/184,924, filed Feb. 25, 2000; Ser. No. 60/190,265, filed Mar. 17, 2000; Ser. No. 60/191,890, filed Mar. 23, 2000; Ser. No. 60/193,586, filed Mar. 30, 2000; Ser. No. 60/197,324, filed Apr. 14, 2000; Ser. No. 60/200,530, filed Apr. 27, 2000; and Ser. No. 60/202,087, filed May 4, 2000.

This application also incorporates by reference the following publications: K. E. van Holde, *Physical Biochemistry* ($2^{nd}$ ed. 1985); William Bains, *Biotechnology from A to Z* (1993); Richard P. Haugland, *Handbook of Fluorescent Probes and Research Chemicals* ($6^{th}$ ed. 1996); Joseph R. Lakowicz, *Principles of Fluorescence Spectroscopy* ($2^{nd}$ ed. 1999); Bob Sinclair, *Everything's Great When It Sits on a Chip: A Bright Future or DNA Arrays*, 13 The Scientist, May 24, 1999, at 18; and Charles R. Cantor and Paul R. Schimmel, *Biophysical Chemistry* (1980).

FIELD OF THE INVENTION

The invention relates to cell signaling. More particularly, the invention relates to assays for detecting the presence and activity of cell-signaling components, including cell-signaling nucleotides.

BACKGROUND OF THE INVENTION

Cellular physiology may be regulated by a variety of mechanisms, originating both inside and outside the cell. In multicellular organisms, these mechanisms may involve cell-signaling pathways in which signal substances are released by one cell to influence the position, nature, and activity of other cells.

FIG. 1 is a schematic view of a representative cell-signaling pathway 100. Here, signaling cells 102 produce signal substances 104a,b that interact with target cells 106 to effect a response in the target cells. These responses may be short term, such as glycogen breakdown or muscle contraction, among others. These responses also may be long term, such as growth, differentiation, reproduction, and/or apoptosis, among others. Generally, these responses are brought about by increasing, decreasing, or maintaining enzyme activity in the target cells.

Signaling cells 102 are cells capable of producing a signal (substance) that can effect a specific response in another (target) cell. The signaling cells may be components of an endocrine, paracrine, or nervous system. The endocrine system is an organism-wide control system that regulates body function using hormones released by endocrine organs into the bloodstream. The endocrine organs include the pituitary gland, thyroid gland, parathyroid glands, adrenal glands, thymus gland, pineal body, pancreas, ovaries, testes, and kidneys. The paracrine system is a local control system that regulates nearby cells using local mediators released into the extracellular medium. The nervous system is a specialized control system that regulates specific cells using electrical impulses and neurotransmitters.

Signal substances 104a,b are substances through which a signaling cell may communicate with target cells, evoking a specific response. Signal substances may act as hormones, local mediators, and/or neurotransmitters, among others. Signal substances may take the form of proteins, small peptides, amino acids, nucleotides, steroids (e.g., cortisol, steroid sex hormones, vitamin D), retinoids, fatty acid derivatives, and dissolved gases (e.g., nitric oxide (NO) and carbon monoxide (CO)), among others.

Target cells 106 are cells capable of responding to a specific signal substance produced by a signaling cell. The ability to respond may depend on the cell and on the signal substance. For example, the signal substance thyroxine from the thyroid gland may evoke a response in nearly all cells, whereas the signal substance progesterone from the ovary may evoke a response only in specific cells in the lining of the uterus. The target response may include kinase activity, GTP binding, and/or cyclic nucleotide production.

The ability of a cell to respond to a given signal substance generally is determined by whether the cell includes a receptor for the signal substance. Here, a receptor is any molecule or supramolecular assembly capable of specifically binding a signal substance and initiating a response in a target cell. Representative receptors include cell-surface receptors 110 located on the surface of the target cell and intracellular receptors 112 located within the cytosol 114 or nucleus 116 of the target cell.

The nature of the response initiated by binding of a signal substance is determined by the intracellular machinery to which the receptor is operatively coupled. For example, binding of the neurotransmitter acetylcholine to identical receptors in heart muscle cells and secretory cells causes muscle relaxation in the heart muscle cells and secretion in the secretory cells, due to differences in the associated intracellular machinery.

The remainder of this section examines (1) the receptor mechanisms that cells use to bind signal substances and to communicate this binding to the cell interior, (2) the intracellular pathways that cells use for regulation, and (3) the effects of errors in cell-signaling pathways.

1. Receptor Mechanisms

Target cells generally have receptors capable of specifically binding specific signal substances, including cell-surface receptors and/or intracellular receptors, as described above. Cell-surface receptors are more common and include (A) G-protein-linked receptors, (B) enzyme-linked receptors, and (C) ion-channel-linked receptors. These receptors typically bind large and/or water-soluble signal substances, such as many peptide hormones. Intracellular receptors are less common and include (A) guanylyl cyclase and (B) ligand-activated gene regulatory proteins. These receptors typically bind small and/or water-insoluble signal substances, such as steroid hormones, thyroid hormones, retinoids, vitamin D, and NO.

FIG. 2 is a schematic view of a representative G-protein-linked cell-surface receptor mechanism 130 that includes a receptor protein 132, a G-protein 134, and a target protein 136. These proteins may be positioned on or within the plasma membrane 138 of a target cell. In use, a specific signal substance 140 binds to a signal-substance binding site 142 on the extracellular side 144 of the receptor protein and thereby creates, exposes, or otherwise activates (*) a G-protein binding site 146 on the intracellular side 148 of the receptor protein. The G-protein then binds to the G-protein binding site on the receptor protein and thereby creates, exposes, or otherwise activates (*) a target-protein binding site 150 on the G-protein. The G-protein then dissociates from the receptor protein, binds (via the target-protein binding site) to the target protein, and activates (*) the target protein. Activation and deactivation of the G-protein may involve binding of a guanosine triphosphate (GTP) molecule and dephosphorylation of the GTP molecule, respectively. The receptor protein may belong to a large superfamily of homologous, seven-pass transmembrane proteins. These seven-pass proteins consist of a single polypeptide chain that crosses the membrane seven times, with an extracellular signal-substance binding portion and an intracellular catalytic portion. The G-protein may be trimeric, consisting of three polypeptide chains—$\alpha$, $\beta$, and $\gamma$—that associate and dissociate during signaling. The target protein may consist of an enzyme or ion channel, among others. In particular, the target protein may be an enzyme that modulates the presence or activity of second messengers within the cell. These second messengers (also known as intracellular messengers or intracellular mediators) may bind allosterically to specific cellular proteins to alter their conformation and hence their activity. These second messengers include adenosine 3',5'-cyclic monophosphate (cAMP) and calcium ($Ca^{2+}$).

In the cAMP pathway, the target protein may be adenylyl cyclase (also known as adenylate cyclase), and the G-protein may be a stimulatory G-protein ($G_s$) that activates the adenylyl cyclase to make cAMP, or an inhibitory G protein ($G_i$) that inhibits the adenylyl cyclase to prevent it from making cAMP. The cAMP produced by the adenylyl cyclase activates cAMP-dependent protein kinase (A-kinase), which is a serine/threonine kinase that in turn activates or inhibits other enzymes to effect a physiological response. For example, in connection with glycogen metabolism, A-kinase may inhibit glycogen synthase to shut down glycogen synthesis, and simultaneously activate phosphorylase kinase that in turn activates glycogen phosphorylase to break down glycogen. A variety of signal substances use cAMP as a second messenger, including calcitonin, chorionic gonadotropin, corticotropin, epinephrine, follicle-stimulating hormone, glucagon, luteinizing hormone, lipotropin, melanocyte-stimulating hormone, norepinephrine, parathyroid hormone (PTH), thyroid-stimulating hormone, and vasopressin. The level of cAMP is reduced by phosphodiesterases, and the activity of kinases is reversed by phosphatases, as described below.

In the $Ca^{2+}$ pathway, the target protein may be a phospholipase with specificity for a phosphoinositide (i.e., inositol phospholipid), and the G-protein may be $G_q$, which activates the phospholipase to cleave the phosphoinositide to produce an intermediate that releases $Ca^{2+}$ from the endoplasmic reticulum. For example, the phospholipase phosphoinositide-specific phospholipase C (phospholipase C-$\beta$) cleaves the phosphoinositide phosphatidylinositol 4,5-bisphosphate ($PIP_2$) to produce the second messengers inositol triphosphate ($IP_3$) and diacylglycerol. The inositol triphosphate is water soluble and diffuses to the endoplasmic reticulum (ER), where it releases $Ca^{2+}$ from the ER by binding to $IP_3$-gated $Ca^{2+}$-release channels in the ER membrane. The diacylglycerol is membrane bound and may be cleaved to form the second messenger arachidonic acid or may activate the $Ca^{2+}$-dependent serine/threonine kinase protein kinase C that in turn activates or inhibits other enzymes to effect a response. A variety of signal substances use $Ca^{2+}$ as a second messenger, including acetylcholine, antigen, thrombin, and vasopressin.

FIG. 3 is a schematic view of a representative enzyme-linked cell-surface receptor mechanism 170 that includes a receptor protein 172 positioned across the plasma membrane 174 of a target cell. The receptor protein includes a signal-substance binding site 176 on the extracellular side 178 of the membrane and a catalytic portion 180 on the intracellular side 182 of the membrane. (In some cases, the catalytic portion of the receptor may be replaced or augmented by a separate enzyme directly associated with the receptor protein.) In use, a specific signal substance 184 binds to the signal-substance binding site, initiating a series of events (such as dimerization and concomitant autophosphorylation of the receptor proteins) that activates (*) the catalytic portion of the receptor. The receptor protein may belong to one of at least five classes of single-pass transmembrane proteins: (A) receptor guanylyl cyclases, which catalyze the production of guanosine 3',5'-cyclic monophosphate (cGMP) in the cytosol; (B) receptor tyrosine kinases, which phosphorylate specific tyrosine residues on some intracellular proteins, (C) tyrosine-kinase-associated receptors, which associate with proteins that phosphorylate specific tyrosine residues on some intracellular proteins; (D) receptor tyrosine phosphatases, which dephosphorylate specific tyrosine residues on some intracellular proteins, and (E) receptor serine/threonine kinases, which phosphorylate specific serine or threonine residues on some intracellular proteins. Some of these receptors are described below in more detail.

The signal substance also may bind to intracellular receptors, such as guanylyl cyclase. This enzyme produces cGMP from GTP, which then acts as a second messenger much like cAMP. As described above, cGMP also may be produced by enzyme-linked cell-surface receptors. cGMP is present in most tissues at levels 1/10 to 1/100 those of cAMP. A variety of compounds increase cGMP levels in cells, including (1) the hormones acetylcholine, insulin, and oxytocin, (2) the guanylate cyclase stimulators (and vasodilators) nitroprusside, nitroglycerin, sodium nitrate, and nitric oxide, (3) chemicals such as serotonin and histamine, and (4) peptides such as atrial natriuretic peptide (ANP) that relax smooth muscle.

2. Intracellular Signaling Pathways

Target cells may have intracellular signaling pathways capable of specifically binding signal substances, including cell-surface receptors and intracellular receptors, as described above. These pathways may include (1) a phosphorylation pathway involving ATP/ADP, and (2) a GTP-binding pathway involving GTP/GDP.

FIG. 4A is a schematic view of a representative phosphorylation pathway. Phosphorylation is the predominant mechanism used to regulate protein activity in eucatyotic cells. In phosphorylation, a phosphate group (P) is reversibly attached to the side chain of an amino acid in a protein. The attached phosphate group may cause structural changes in the protein, for example, due to electrostatic interactions between the negative charges on the phosphate group and positive charges on the side chains of nearby amino acids. These structural changes may affect the activity of the phosphorylated protein, enhancing or inhibiting its function.

Specialized enzymes control phosphorylation in cells. In particular, protein kinase enzymes transfer phosphate groups to proteins, and protein phosphatase enzymes remove phosphate groups from proteins. Protein kinases and protein phosphatases are found in great variety in eucaryotic cells: a single cell may contain more than 100 different kinases, and one percent of genes may code for kinases.

There are two major categories of kinases: (1) serine/threonine (S/T) kinases, and (2) tyrosine kinases. The S/T kinases function by selectively phosphorylating serine and threonine side chains on substrate proteins or peptides. These kinases include cyclic AMP-dependent kinase (A-kinase), cyclic GMP-dependent kinase (G-kinase), protein kinase C (C-kinase), $Ca^{2+}$-calmodulin-dependent kinase (CaM-kinase), phosphorylase kinase, MAP kinase, and TGF-$\beta$ receptor, among others. The S/T kinases are predominantly cytosolic. The tyrosine kinases function by selectively phosphorylating tyrosine side chains on substrate proteins or peptides. These kinases include the receptor kinases for epidermal growth factor (EGF), platelet-derived growth factor (PDGF), fibroblast growth factors (FGFs), hepatocyte growth factor (HGF), insulin, insulinlike growth factor-1 (IGF-1), nerve growth factor (NGF), vascular endothelial growth factor (VEGF), and macrophage colony stimulating factor (M-CSF). These kinases also include the nonreceptor kinases associated with the tyrosine-kinase-associated receptors, such as the Src family (Src, Yes, Fgr, Fyn, Lck, Lyn, Hck, and Blk) and Janus family (JAK1, JAK2, and Tyk2) kinases. The tyrosine kinases are predominantly membrane bound. A few kinases function by selectively phosphorylating threonine and tyrosine side chains on substrate proteins or peptides. These kinases include the mitogen-activated protein (MAP) kinase-kinase.

FIG. 4B is a schematic of a representative GTP-binding pathway. The GTP-binding pathway generally resembles the phosphorylation pathway in that each pathway involves transfer of a phosphate group to a protein. However, in the GTP-binding pathway, the protein gains a phosphate group by exchanging a bound GDP for a bound GTP, whereas in the phosphorylation pathway, the protein gains a phosphate group by covalent addition of the phosphate group to a serine, threonine, or tyrosine by a kinase enzyme. The binding of a GTP to a GTP-binding protein may cause structural changes in the protein that in turn affect the activity of the protein. Examples of GTP-binding proteins include the trimeric G-proteins described above and the Ras superfamily of monomeric GTPases. The Ras proteins are activated by release of bound GDP and binding of GTP stimulated by guanine-nucleotide releasing proteins (GNRPs). The Ras proteins are inactivated by hydrolysis of the bound GTP by GTPase-activating proteins (GAPs).

A physiological response may require stimulation by only a single type of signal substance, or may require stimulation by two or more types of signal substances. The latter mechanism permits finer tuning of the physiological response through signal integration. For example, a protein may be activated only by phosphorylation by two different kinases, themselves activated by binding of two different signal substances to two different receptors. Alternatively, a protein may be activated only by concurrent phosphorylation and GTP binding, or by binding of two subunits whose binding is contingent on phosphorylation by separately activated kinases.

3. Effects of Errors

Errors in the signal transduction and regulation pathways described above can cause cancer and other diseases. Indeed, a primary cause of cancer is a mutation that makes a stimulatory gene product hyperactive, converting a proto-oncogene into an oncogene. The primary classes of known proto-oncogenes include the following cell-signaling proteins: (1) growth-factor receptors acting via tyrosine kinases, (2) GTP binding proteins, (3) membrane/cytoskeleton-associated tyrosine kinases, (4) cytoplasmic tyrosine kinases, (5) steroid-type growth-factor receptors, and (6) S/T kinases. Consequently, cell-signaling proteins have become important subjects of research and drug development.

Assays that determine the presence and activity of cell-signaling components are important tools for high-throughput screening laboratories. Unfortunately, current assays have a number of shortcomings. For example, the presence and activity of kinases can be determined using assays capable of detecting phosphorylated amino acids. In a standard kinase assay, radioactive ATP and an appropriate protein substrate are added to a sample. If the sample includes kinases, radioactive phosphate groups will be transferred from the radioactive ATP to the protein substrate. The protein substrate and radioactive ATP can be separated, and the presence and activity of kinases determined by assaying the amount of radioactive protein substrate. Unfortunately, this assay involves radioactivity, presenting a short-term safety hazard for the assay operator and a long-term storage and disposal problem. Moreover, the assay is heterogeneous, requiring separation of components for analysis. Significantly, assays for other cell-signaling components may have similar shortcomings, as well as slow time courses and unstable endpoints that require precise timing of assay readouts. Thus, there is a need for improved assays for detecting the presence and activity of cell-signaling components.

SUMMARY OF THE INVENTION

The invention provides improved assays for detecting the presence and activity of cell-signaling components. These assays include luminescence polarization assays for detecting cell-signaling nucleotides and modulators of receptors and enzymes related to the production and activity of such nucleotides.

BRIEF DESCRIPTION OF THE DRAWINGS

FIG. 4 is a schematic view of two common intracellular signaling pathways: (A) a phosphorylation pathway involving ATP/ADP, and (B) a GTP-binding pathway involving GTP/GDP.

FIG. 5 is a schematic view of a cyclic nucleotide assay in accordance with aspects of the invention.

FIG. 6 is a schematic view of a GTP-binding protein assay in accordance with aspects of the invention.

FIG. 7 is a view of representative cAMP tracers constructed in accordance with aspects of the invention: (A) fluorescein-ITC-1,4-DACHsuccinimidyl cAMP and fluorescein-ITC-1,2-DACHsuccinimidyl cAMP, and (B) carboxyfluorescein-ITC-1,4-DACHsuccinimidyl cAMP and carboxyfluorescein-ITC-1,2-DACHsuccinimidyl cAMP.

FIG. 8 is a view of representative cGMP tracers constructed in accordance with aspects of the invention: (A) fluorescein-ITC-1,4-DACHsuccinimidyl cGMP and fluorescein-ITC-1,2-DACHsuccinimidyl cGMP, and (B) carboxyfluorescein-ITC-1,4-DACHsuccinimidyl cGMP and carboxyfluorescein-ITC-1,2-DACHsuccinimidyl cGMP.

FIG. 9 is a schematic view of a microplate showing a well layout for a cAMP assay, including positions of samples, calibrators, and controls: (A) well layout page 1, and (B) well layout page 2.

FIG. 12 is a graph showing another application of a cAMP assay to detection of adenylyl cyclase activity in a membrane preparation.

FIG. 13 is a graph showing an application of the cAMP assay to the effects of modulators in a whole cell preparation.

DETAILED DESCRIPTION

Figure 1:
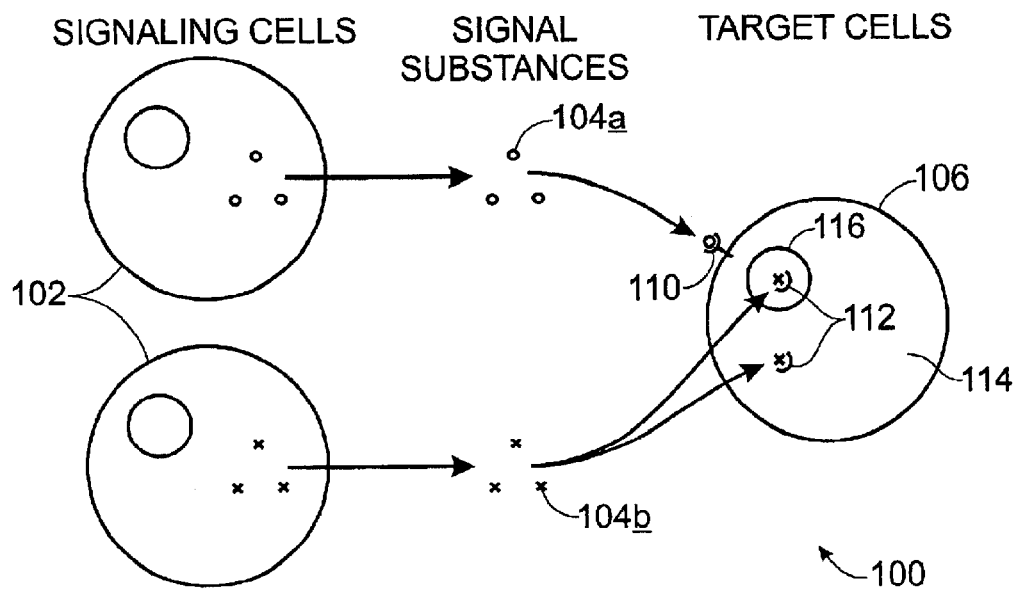
FIG. 1 is a schematic view of a cell-signaling pathway.
Figure 2:
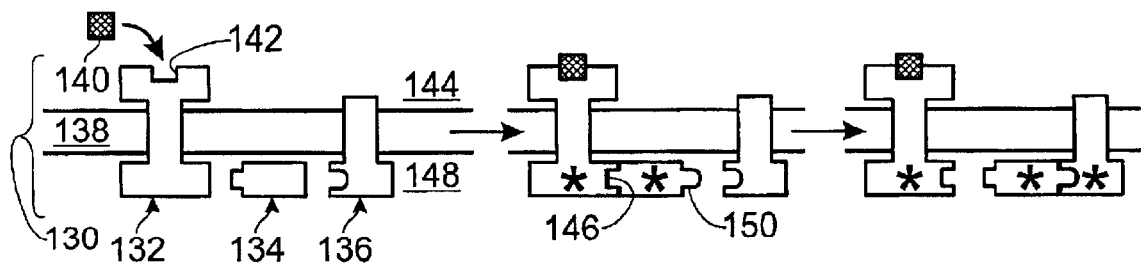
FIG. 2 is a schematic view of a G-protein-linked cell-surface receptor mechanism that includes a receptor protein, a G-protein, and a target protein, all associated with the plasma membrane of a target cell.
Figure 3:
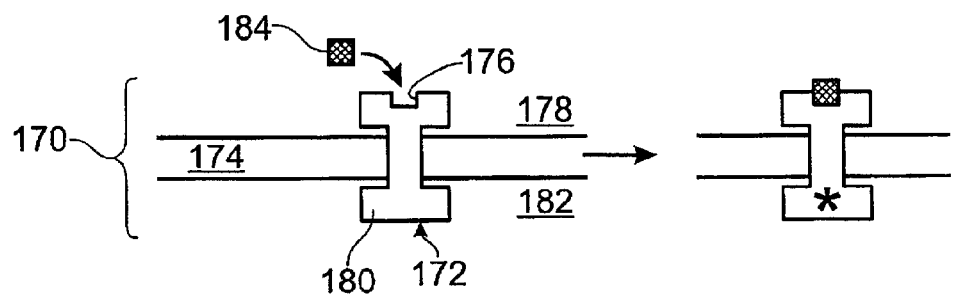
FIG. 3 is a schematic view of an enzyme-linked cell-surface receptor mechanism that includes a receptor protein positioned across the plasma membrane of a target cell.

The invention provides improved assays for detecting the presence and activity of cell-signaling components. These assays include among others luminescence polarization assays for detecting cyclic nucleotides and modulators of receptors and enzymes related to the generation and activity of cyclic nucleotides, such as GTP-binding proteins.

FIG. 5 is a schematic view of a cyclic nucleotide assay provided by the invention. Here, a sample containing a cyclic nucleotide (analyte) is contacted with a luminescent tracer and a binding partner capable of specifically and competitively binding the cyclic nucleotide and the luminescent tracer. Suitable analytes, tracers, and binding partners are described below; representative examples include cAMP and cGMP, luminescently labeled cAMP and cGMP, and anti-cAMP and anti-cGMP antibodies, respectively. The analyte will reduce the amount of tracer bound to the binding partner, because the analyte will compete with the tracer for the limited number of binding sites associated with the binding partners. The change in free and bound tracer can be monitored using luminescence polarization. Free tracer is small and will tumble or reorient rapidly relative to the luminescence lifetime, so that it will emit relatively depolarized light in response to excitation with polarized light. In contrast, bound tracer is large and will tumble or reorient more slowly relative to the luminescence lifetime, so that it will emit relatively polarized light in response to excitation with polarized light. Thus, the extent of polarization will be inversely correlated with the concentration of analyte, and the displacement of the tracer from the binding partner by the analyte will result in a decrease in polarization.

The invention provides luminescence-based methods for determining the concentration of various cyclic nucleotides. Such methods may include (1) contacting a sample in which the concentration of a cyclic nucleotide is to be measured with a luminescent tracer and with a specific binding partner capable of specifically and competitively binding the cyclic nucleotide and tracer, (2) illuminating the sample with polarized light, where the light is capable of inducing emission of polarized light from the tracer, (3) measuring the extent of polarization of light emitted from the tracer, and (4) correlating the extent of polarization of the emitted light with the concentration of the cyclic nucleotide.

The invention also provides methods for identifying modulators of receptors and/or enzymes involved in the generation of cyclic nucleotides. Such methods may include looking for the effects of such a modulator by conducting a method for determining the concentration of a cyclic nucleotide (such as that described above) in both the presence and absence of the putative modulator. In this approach, an increase in the measured extent of polarization of the emitted light in the presence of the putative modulator identifies the putative modulator as an inhibitor of the receptor or enzyme, and a decrease in the measured extent of polarization in the presence of the putative modulator identifies the putative modulator as an agonist of the receptor or enzyme.

Stated differently, the concentration of a signaling intermediate (e.g., a cyclic nucleotide) may be used as an index to the activity of the enzyme(s) (directly or indirectly) catalyzing production of the intermediate, or as an index to an agonist with regard to that activity or an inhibitor with regard to that activity. If the enzyme is associated with a receptor, the assay effectively measures the ability of a candidate or test compound to act as an agonist or antagonist of the receptor, modulating activity of the receptor. Thus, the assays of the invention provide a broad spectrum of assessment to evaluate cell-signaling, metabolism, catalytic activities, and protein synthesis.

FIG. 6 is a schematic view of a GTP-binding protein assay provided by the invention. Here, a sample containing a putative modulator of a GTP-binding protein is contacted with a GTP-binding protein, GDP, and a luminescent GTP tracer. If the modulator activates (*) the GTP-binding protein, the GDP will be released, and the GTP tracer will be bound. In a polarization assay, the polarization of light emitted by the tracer will increase upon such binding, because the rotational mobility of the GTP tracer will be reduced. This increase may be used to assay for the extent of binding and hence the activity or effectiveness of the putative modulator.

Samples and assay components such as tracers and binding partners may be brought into contact using any method for effectuating such contact. A preferred method is by mixing the materials in solution, although other methods, such as attaching one or more components to a bead or surface, also may be used, as long as the components retain at least some specificity and binding affinity following such attachment.

Samples may be supported for analysis by any substrate or material capable of providing such support. Depending on the embodiment, suitable substrates include microplates, PCR plates, biochips, and hybridization chambers, among others, where features such as microplate wells and biochip array sites may comprise assay sites. Preferred microplates are described in the following U.S. Patent Applications, which are incorporated herein by reference: Ser. No. 08/840,553, Ser. No. 09/156,318, and Ser. No. 09/478,819. These microplates may include 96, 384, 1536, or other numbers of wells. These microplates also may include wells having elevated bottoms, small ($\geq 50$ μL) volumes, and/or frustoconical shapes capable of matching a sensed volume. Preferred PCR plates may include the same (or a similar) footprint, well spacing, and well shape as the preferred microplates, while possessing stiffness adequate for automated handling and thermal stability adequate for PCR. Preferred DNA arrays are described in Bob Sinclair, *Everything's Great When It Sits on a Chip: A Bright Future for DNA Arrays,* 13 The Scientist, May 24, 1999, at 18. Preferred hybridization chambers are described in PCT Patent Application Serial No. PCT/US99/03678, which is incorporated herein by reference.

Samples may be illuminated and light from samples may be detected using any suitable light detection device, particularly one capable of inducing and detecting polarized emission from the sample. Preferred light detection devices include a high color temperature light source and are capable of illuminating and/or detecting light substantially exclusively from a sensed volume within the sample. Additional features of the preferred light detection devices, including apparatus and detection methods, are described in the following U.S. Patent Applications, which are incorporated herein by reference: Ser. Nos. 09/160,533, and 09/349,733.

The extent of polarization of light emitted from the sample may be correlated with the concentration of cyclic nucleotide and/or the presence and/or identity of a modulator of a receptor or enzyme that generates a cyclic nucleotide using various methods. A preferred method is to compute a polarization or anisotropy function following a competition assay, wherein the polarization and anisotropy of the emitted light are inversely correlated with the concentration of the cyclic nucleotide. Apparatus and methods for creating, detecting, and/or interpreting results obtained using polarized light are described in the Examples that appear below and in the following patent applications, which are incorporated herein by reference: U.S. patent application Ser. No. 09/349,733, and U.S. Provisional Patent Application Ser. No. 60/182,419.

The assays provided by the invention may have various advantages over prior assays for detecting cyclic nucleotides. First, they may be used without radioactivity. Second, they may be homogenous, so that they do not require physical separation steps or wash steps. Third, they may have stable endpoints, so that results are relatively insensitive to the timing of any measurement or detection steps. Fourth, they may be sensitive, so that pmol amounts of cyclic nucleotides may be detected. Fifth, they may be used with solution and cell-based samples.

Further aspects of the invention are described without limitation in the patent applications and other materials incorporated by reference under Cross-References and in the following sections: (A) Assay Components, and (B) Examples.

A. Assay Components

The invention in its various aspects may include and/or involve among others one or more of the following: (1) analytes, (2) tracers, (3) specific binding partners, and (4) modulators. The format of the assay may place constraints on the preferred relative concentrations of analyte, tracer, and specific binding partner and on the preferred lifetime of the luminophore associated with the tracer. For example, in a competition assay, the concentration of binding partner is preferably at least about equal to the concentration of tracer (to permit stoichiometrically an appreciable fraction of the tracer to be bound), and the affinity of the binding partner for the tracer is preferably such that the dissociation coefficient $K_d$ describing interaction between the binding partner and tracer is about equal to the concentration of the free binding partner (so that the fraction of bound tracer is not too close either to 0 or 1, to maximize sensitivity). Moreover, the lifetime of the luminophore associated with the tracer preferably is longer than the rotational correlation time of free tracer and shorter than the rotational correlation time of bound tracer, and, all else being equal, ideally equal to the geometric mean of the two rotational correlation times of free and bound tracer (to obtain the largest polarization change upon binding).

1. Analytes

The analyte generally comprises any compound or other species whose presence, concentration, and/or activity is to be assayed. For example, the analyte in a cyclic nucleotide assay is a cyclic nucleotide, such as the following:

| Abbreviation | Definition |
|---|---|
| cAMP | Adenosine cyclic monophosphate |
| cCMP | Cytidine cyclic monophosphate |
| cGMP | Guanosine cyclic monophosphate |
| cTMP | Thymidine cyclic monophosphate |
| cUMP | Uridine cyclic monophosphate |

Preferred cyclic nucleotide analytes include cAMP and cGMP, which are used by cells as second messengers in various intracellular signaling pathways.

An analyte may be one of several components in a sample being analyzed. A sample generally comprises any composition in which the concentration of analyte is to be measured, and/or in which the presence and/or identity of a modulator of receptors or enzymes that generate the analyte is to be measured. The sample may be natural, artificial, or a combination thereof, and may include compounds, compositions, mixtures, surfaces, solutions, emulsions, suspensions, cells, cell cultures, fermentation cultures, tissues, secretions, and/or derivatives and/or extracts thereof, among others. Assays of purified enzyme, cell lysates, and so on generally will require optimization and validation based upon the requirements of the individual test systems.

2. Tracers

The tracer generally comprises any luminescent compound or other species capable of competing with the analyte for binding to a specific binding partner. A preferred tracer may be the analyte itself coupled to a luminophore. For example, in a cyclic nucleotide assay, a preferred tracer is a cyclic nucleotide coupled to a luminophore.

The luminophore may include any compound capable of emitting light in response to excitation with light, and more particularly of emitting polarized light in response to excitation with polarized light. Suitable luminophores are described in Richard P. Haugland, *Handbook of Fluorescent Probes and Research Chemicals* ($6^{th}$ ed. 1996), which is incorporated herein by reference. Preferred luminophores include xanthene dyes such as fluorescein and various rhodamines, BODIPY™ dyes, cyanine dyes such as CY-5™, and others, including luminophores described in patent applications listed above under Cross-References, which are incorporated herein by reference.

The luminophore may be coupled to the analyte covalently or noncovalently. Luminophores may be coupled covalently (for example, to the 2' hydroxyl) using various reactive groups, including amines, carboxylic acids, isothiocyanates, hydrazides, thiols, maleimides and dichlorotriazinyl derivatives. Luminophores may be coupled noncovalently using various specific binding pairs, including avidin and biotin, protein A and immunoglobulins, and lectins and sugars (e.g., concanavalin A and glucose). In preferred polarization tracers, the luminophore is coupled to the analyte by a rigid coupling group, such as a diaminocyclohexyl coupling group.

Preferred tracers will undergo a significant change in polarization upon binding to a preferred binding partner, and will have high extinction coefficients, intrinsic polarizations, quantum yields, and/or Stokes' shifts.

3. Specific Binding Partners

The specific binding partner generally comprises any compound capable of specifically and competitively binding an analyte and an associated tracer. Specific binding means binding to the specific binding partner to the exclusion of binding to most other moieties. Specific binding can be characterized by a binding coefficient. Generally, specific binding coefficients range from $10^{-4}$ M to $10^{-12}$ M and lower, and preferred specific binding coefficients range from $10^{-9}$ M to $10^{-12}$ M and lower.

In some assays, fragments, derivatives, or analogs of a preferred specific binding partner may be used, if such fragments, derivatives, and analogs retain their specificity and binding affinity for their binding partners. In other assays, such fragments, derivatives, and analogs, or the specific binding partners themselves, may be coupled to solid supports or other moieties, including beads and walls.

Preferred specific binding partners include immunological specific binding partners, such as antibodies. Such preferred binding partners will bind to the cyclic nucleotide of interest, independent of whether the cyclic nucleotide is coupled to a luminophore. However, such coupling may affect the coefficient of such binding. Immunological binding partners include polygonal and monoclonal antibodies. Immunological binding partners also include chimeric, single chain, and humanized antibodies, as well as Fab fragments and the products of Fab expression libraries.

Immunological binding partners, including antibodies and fragments, analogs, and/or derivatives of such antibodies, can be prepared by various generally known procedures. For example, antibodies against cyclic nucleotides can be obtained by injecting or otherwise administering a suitable immunogen into an animal. Suitable immunogens may include the cyclic nucleotide itself, fragments, analogs, and/or derivatives thereof, or cells expressing such cyclic nucleotides, fragments, analogs, and/or derivatives. The antibody so obtained should specifically bind to the cyclic nucleotide.

Monoclonal antibodies can be prepared by any technique that provides antibodies produced by continuous cell line cultures. Examples include the hybridoma technique (Köhler and Milstein, Nature 256:495 (1975)), the trioma technique, the human B-cell hybridoma technique (Kozbor et al., Immunology Today 4:72 (1983)), and the EBV-hybridoma technique to produce human monoclonal antibodies (Cole et al., in Monoclonal Antibodies and Cancer Therapy, Alan R. Liss, p. 77 (1985)).

Single-chain antibodies can be prepared using any technique for producing single-chain antibodies. Examples include the method described in U.S. Pat. No. 4,946,778.

4. Modulators

The modulator generally comprises any compound or other species capable of modulating the activity of receptors, enzymes, and/or other species involved in the generation of analyte. The modulator may be an agonist or an inhibitor of analyte production, meaning that it may promote or inhibit analyte production. For example, in a cyclic nucleotide assay, preferred agonists include forskolin and isoproterenol, and preferred inhibitors include propranolol.

B. EXAMPLES

The following examples are intended to illustrate without limitation various aspects of the invention.

Example 1

This example shows representative tracers for use in cyclic nucleotide assays, and particularly luminescence-polarization-based cyclic nucleotide assays. General structures for such tracers are shown below for (A) cAMP and (B) cGMP:

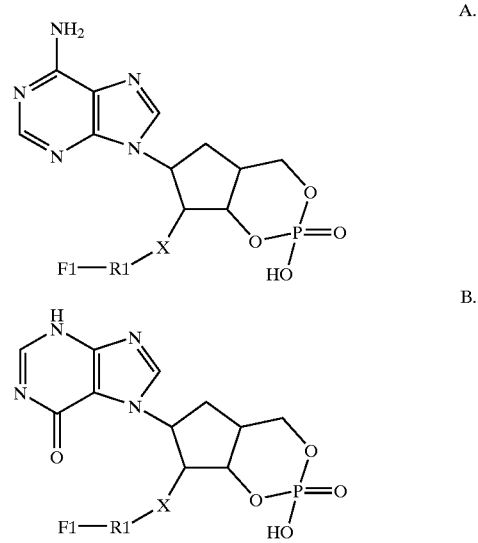

X can be any alkyl, allyl, or aryl linker with ester or ether bonds to the cyclic nucleotide, including —OC(=O)— CH$_2$CH$_2$C(=O)—. R1 can be a rigid linker that provides (two) reactive groups for coupling, one to the nucleotide and another to the group F1. In particular, R1 can be a diaminoalkyl, -cycloalkyl, -aryl, or -allyl group, or a dihydroxy group, that forms an amide or ester, respectively, with the groups X and F1. F1 can be any luminophore suitable for polarization, such as fluorescein or a rhodamine, that forms a thiourea, ester, or amide bond with the group X. Preferred structures include 1,2 and 1,4-diaminocyclohexyl-linked tracers, as shown in FIG. 7 for cAMP and FIG. 8 for cGMP.

Example 2

This example shows a mechanism for producing specific binding partners. Specifically, antisera to cAMP were produced by conjugating 2'o-succinyl-cyclic 3',5' adenosine monophosphate to the carrier KLH using standard methods, and using this conjugate as an immunogen. Preparation of antisera in rabbits was done according to an enhanced method of antibody production, using low (25 µg per injection) doses of immunogen to enhance the immune response. Antisera obtained using this approach were superior to commercial antisera.

Example 3

This example shows a method (and associated kit) for detecting cAMP and modulators of receptors and enzymes that generate cAMP. Specifically, the assay is designed for use in applications where cAMP is generated or consumed, such as adenylyl cyclase or phosphodiesterase assays. The assay may be used to detect cAMP or the activity of adenylyl cyclase or phosphodiesterase, among others, through their effect on cAMP concentration, via a competitive luminescence-polarization immunoassay. The assay is homogeneous, requiring no separation or wash steps, and can be completed in two hours. The cAMP product of an adenylyl cyclase reaction (or substrate of a phosphodiesterase reaction, or calibrators, or controls) competes with a fluorescein-labeled cAMP tracer (fluorescein-5-ITC-DACHsuccinimidyl-cAMP) for binding sites on anti-cAMP antibodies. In the absence of cAMP, most of the tracer is bound to the antibody. However, in the presence of cAMP, the amount of bound tracer decreases competitively with increasing concentrations of cAMP. The rate of molecular rotation of the tracer is much lower when the tracer is bound to antibody than when it is free in solution, so that the polarization of light emitted by the tracer is higher when the tracer is bound to antibody than when it is free. Thus, the polarization decreases as the amount of bound tracer decreases, allowing a quantification of the analyte cAMP, and hence any species that creates or degrades it.

1. Materials

Reagents may be provided separately or bundled together as a kit. A preferred kit includes anti-cAMP antibody (100×), cAMP tracer (fluorescein-labeled cAMP, 100×), calibrator cAMP (500 mM), and assay buffer.

| Reagent/Buffer | Stock Concentration | Final Concentration in Assay Plate |
|---|---|---|
| cAMP calibrator (1 vial) | 1 mM | 1:3 serial dilution in assay plate: 10, 3.33, 1.11, 0.37. 0.12, 0.041, 0.014, & 0.005 µM |
| cAMP antibody (1 vial) | 300× | 1:300 dilution in assay plate |
| cAMP tracer (1 vial) | 500× | 1:500 dilution in assay plate |
| Assay buffer (pH 7.6) | | |

The assay buffer should be stored refrigerated at 4° C., and the remaining reagents should be stored frozen at ≦−10° C. For optimal performance, the antibody should not undergo repeated freeze/thaw cycles, and the tracer should be protected from light. All reagents should be warmed to room temperature before use.

The tracer may be titrated before use to determine the optimal working dilution for each application. The recommended dilution provides an intensity reading 5 to 6-fold higher than the assay buffer background and allows the kit to be used for two 384-well microplates with 40 µL total assay volume per well or two 96-well microplates with 100 µL total assay volume per well.

2. Equipment

The assay may be performed using any suitable sample holder, light detection device, and/or fluidics system, as described above. A preferred sample holder (for supporting samples) is a microplate, particularly a COSTAR™ flat-bottom black microplate (Corning) or an LJL HE™ black microplate, among others. A preferred light detection device (for analyzing samples) is an ANALYST™ light-detection platform (LJL BioSystems, Inc.). A preferred fluidics system (for preparing samples) is an LJL ScreenStation™, as described in PCT Patent Application Serial No. PCT/US00/12277, which is incorporated herein by reference.

3. Procedure

The following procedure uses 100 wells of a 384 well plate, with calibrators and controls occupying up to 32 of the wells:

(1) Preparation of reagents and samples:

(a) Preparation of 1:75 cAMP antibody working stock. Dilute the 300×cAMP antibody stock 1:75 in cAMP assay buffer (0.05 M HEPES, pH 7.5, 150 mM NaCl, 0.1% bovine gamma globulin) (e.g., by adding 14 µL of the 300×cAMP antibody stock to 1036 µL of cAMP assay buffer). 10 µL of this working stock solution will be added to the assay plate, as indicated in the plate layout in FIG. 9.

(b) Preparation of cAMP tracer working stock. Dilute the 500×cAMP tracer stock 1:125 in cAMP assay buffer (e.g., by adding 10 µL of the 500×cAMP tracer stock to 1240 µL of cAMP assay buffer). 10 µL of this working stock solution will be added to the assay plate, as indicated in the plate layout in FIG. 9.

(c) Preparation of cAMP calibration curve. Dilute the cAMP calibrator 1:25 in cAMP assay buffer (e.g., by adding 10 µL cAMP calibrator to 240 µL cAMP assay buffer) to give 10 µM cAMP calibrator or 400 pmol in final assay. Prepare seven 1:3 serial dilutions to give 3.33, 1.11, 0.37, 0.12, 0.041, 0.014, and 0.005 µM cAMP (133 to 0.125 pmol in final assay).

(d) Preparation of samples. Dilute samples as needed in cAMP assay buffer. Prepare at least 25 µL of each dilution if duplicates are to be run.

(2) Addition of calibrators, controls, and samples to 384-well plates.

Add calibrators, controls, and samples to the assay plate, as indicated in the plate layout in FIG. 9. Preferably, titrations should be performed in duplicate, and controls should be performed in quadruplicate. Order of addition and incubation time are very important.

(a) Add cAMP assay buffer to respective wells.

(b) Add cAMP working stock antibody to respective wells.

(c) Add cAMP calibrator or sample to respective wells.

(d) Add tracer to respective wells, mix gently, cover, and incubate for 2 hours, shielded from room light. To further increase assay performance, incubate the assay plate overnight at 4° C., covered and shielded from light. A plastic plate cover may be used to prevent possible evaporation, but care should be taken with plastic plate sealers, which may introduce undesirable background fluorescence.

(e) Read plate using a light detection device capable of generating and detecting polarized light. A preferred light detection device is an ANALYST™ light-detection platform, used with the following parameter settings:

| Parameter | Setting |
| --- | --- |
| Lamp | Continuous |
| Plate format | Corning Costar 384 PS |
| Wells selected | (Select data range) |
| Z-height | 2 mm |
| G-factor | 0.94 (depending on instrument) |
| Units | Counts/sec |
| Excitation | 1 Fluorescein 485 nm |
| Emission | 1 Fluorescein 530 nm |
| Reading per well | 1 |
| Integration time | 200,000 |
| Attenuator mode | Out |
| Dynamic polarizer | Emission |
| Static polarizer | S |
| Polarizer settling time | 10 ms |
| Shake time | 0 sec |
| Velocity | 20 mm/sec |
| Diameter | 5 mm |
| Measurement type | Comparator (sensitivity = 2–4) |
| Plate settling time | 50 ms |

(f) Calculate background-corrected P values if desired, and plot mP vs. pmol cAMP calibration curve, as described below.

4. Data Analysis

The data for the calibration curve can be analyzed using any suitable method, such as importing the data into an Excel spreadsheet for analysis. To improve accuracy, polarizations should be computed using corrected sample intensities determined by subtracting background intensities from the raw sample intensities, and not by computing raw sample polarizations and then subtracting background polarizations. A preferred procedure is described below.

(1) Average both "S" and "P" intensity readings for the assay buffer alone (wells 2A–D) and antibody alone (wells 2J–L). These are the "buffer background" and "antibody background" values, respectively.
(2) Subtract the "S" buffer background value from each individual "S" value for the tracer (column 2, I–L, tracer only). Repeat to correct the "P" intensity values of the tracer.
(3) Subtract the "S" antibody background value from each individual "S" value for the tracer bound to the antibody (column 2, E–H) and from each of the values for the calibration curve and samples (columns 1 & 3). Repeat to correct the "P" intensity values for the above measurements.
(4) Calculate the polarization (in milli-polarization "mP" units) for the background-corrected data for columns 1, 2 (tracer only and tracer+antibody), and 3 using the following formula:

$$P = \frac{S - (G \cdot P)}{S + (G \cdot P)} \cdot 1000 \; [\text{mP}] \quad (1)$$

Here, G is a "G factor," which corrects for contributions of the instrument light path to total polarization. In practice, G is almost always close to unity, so it usually can be conveniently set to this value without compromising the subsequent analysis.

(5) Average the individual values for columns 1, 2 (tracer only and tracer+antibody), and 3.
(6) Plot the calibration curve. Calculate the IC50 concentration (i.e., the concentration of the calibrator that gives a 50% decrease in polarization from bound vs. free tracer), either from the data or from the calibration curve.

Example 4

Figure 10:
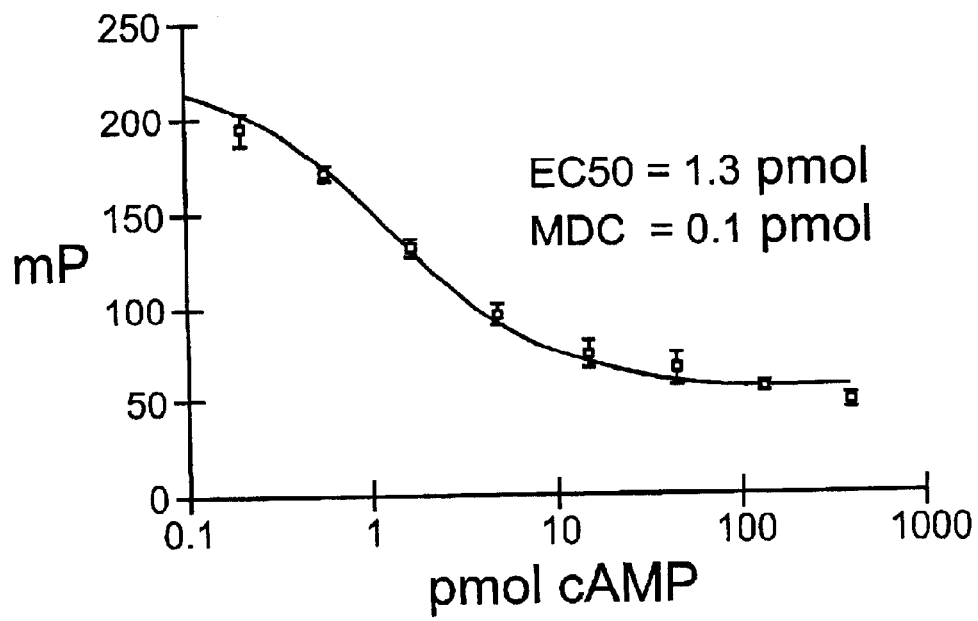
FIG. 10 is a calibration curve for a cAMP assay.

This example shows use of a calibration curve in a cAMP assay. Specifically, FIG. 10 shows a calibration curve for a cAMP assay measured using the reagents and methods of Example 4. The polarization of the calibrator was computed after subtracting the appropriate background intensities, as described above. The cAMP concentration in an unknown sample is determined by matching the polarization measured for the unknown with the cAMP concentration corresponding to that polarization in the calibration curve. The minimum detectable concentration was about 0.1 pmol.

Example 5

Figure 11:
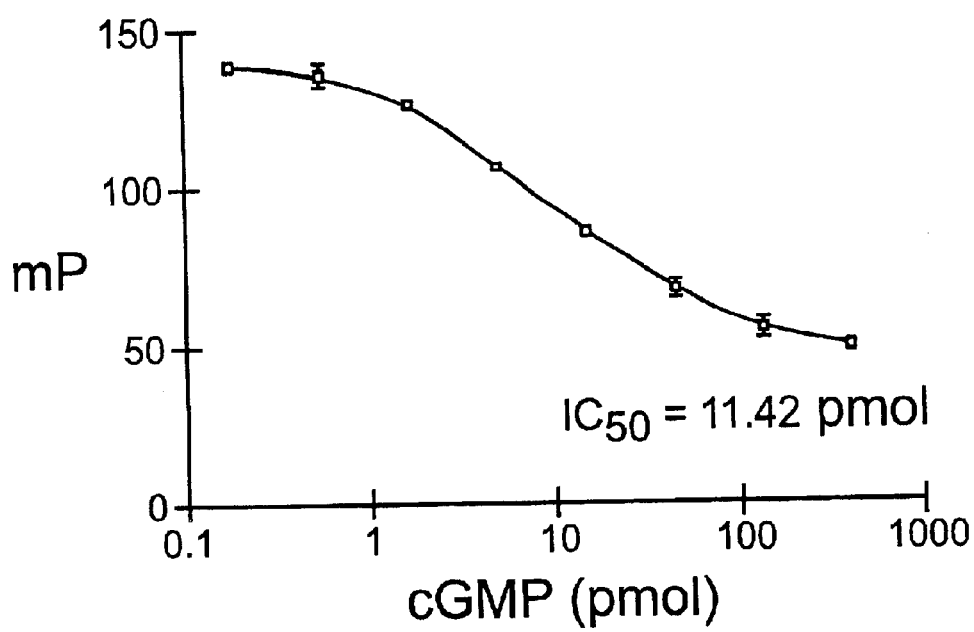
FIG. 11 is a calibration curve for a cGMP assay.

This example shows use of a calibration curve in a cGMP assay. Specifically, FIG. 11 shows a calibration curve for a cGMP assay conducted using cGMP-based reagents and methods analogous to those described (for cAMP) in Example 4. The cGMP concentration in an unknown sample is determined by matching the polarization measured for the unknown with the cGMP concentration corresponding to that polarization in the calibration curve. Here, the tracer is fluorescein-5-ITC-1,4-diaminocyclohexyl-2'-O-succinyl-GMP, and the specific binding partner is an anti-cGMP antibody (Chemicon). The calibration curve shows that the change in polarization obtained using these reagents is smaller than the change in polarization obtained under similar conditions in FIG. 10 for cAMP; however, this change may be increased by using different reagents, such as the tracer 1,2-diaminocyclohexyl (DACH).

Example 6

This example shows another assay for adenylyl cyclase activity. Specifically, FIG. 12 shows activity of recombinant adenylyl cyclase in membrane preparations, measured using (A) the reagents and methods of Example 3, and (B) a standard radioactivity-based assay (FlashPlate™ assay, New England Nuclear). The results show that the present assay performs well in comparison with standard radioactivity-based assays.

Example 7

This example shows an assay for phosphodiesterase activity. Specifically, in a sample provided with a luminescent cAMP (or other cyclic nucleotide) tracer and a specific binding partner, phosphodiesterase will hydrolyze the cAMP to the corresponding monophosphate, which should no longer bind to the specific binding partner. This will decrease the amount of tracer bound to the binding partner and concomitantly decrease the measured polarization.

Example 8

This example shows a method (and associated kit) for detecting cAMP and modulators of receptors and enzymes that generate cAMP in whole cells. The following two protocols illustrate with the general adenylate cyclase activator forskolin an application of this assay, which may be applied in combination with the assay of Example 3. The protocols have been developed for use with adherent or suspension cells. The procedure could be modified for agonists or antagonists such as the beta-adrenergic agonist isoproterenol or antagonist propranolol. FIG. 13 illustrates both forskolin and agonists/antagonist detection for a typical assay. Forskolin causes the expected rise in cAMP in the adherent cell line T47D (following the protocol below for adherent cells). The beta-adrenergic agonist isoproterenol also stimulates cAMP production, via the endogenous beta receptors on the cells. This stimulation is reversed by addition of a beta adrenergic antagonist, propranolol.

(1) Adherent Cells

The following example is for adherent cells, for example, using the adherent cell line T-47D:

1) Culture cells (100 μL/well) in standard 96-well microtiter plates (tissue culture grade) with cell concentration at 2.5–10×10$^5$ cells/mL (25,000–100,000 cells/well).
2) Incubate plated cells overnight at 37° C. in a humidified atmosphere of 5% $CO_2$:95% air.
3) Gently aspirate off media, and slowly add 250 μL Krebs-Ringer Bicarbonate Buffer with glucose, pH 7.4 (KRBG Buffer); use multi-channel pipettor.
4) Gently aspirate off the KRBG and add 100 μL Stimulation Buffer
    Stimulation Buffer (containing 0.75 mM IBMX in KRBG Buffer; make fresh on day of experiment).
    10 mL KRBG Buffer (pH 7.4)
    9.4 μL 800 mM IBMX
5) Incubate for 10 minutes at room temperature.
6) Add 50 μL 3×Forskolin or PBS. Gently mix and incubate at 37° C. for 15 minutes.
    Forskolin, 3×(20 μM final concentration)
    1500 μL PBS (pH 7.4) containing
    3.0 μL 30 mM forskolin (60 μM stock)
7) Add lysis reagent, 4×Ly×Buffer (50 μL). Agitate cells. This is to facilitate cell lysis and can be achieved by shaking the plate on a plate shaker for 10 minutes after adding the lysis reagent.
    4×Ly×Buffer
    2% tritonx–100
    0.1% acetic acid
8) Lysed cells are now immediately processed in the HEFP cAMP assay, using 10 μL neat, or suitably diluted in additional 1×Ly×lysis buffer.

(b) Suspended Cells

The following example is for cells in suspension, for example, using the cell line HEK 293. Cells are treated with 0.02% EDTA to gently detach cells. The entire assay (cell stimulation, lysis, and cAMP assay) was performed in a single 384-well plate:

1) Grow cells in T-75 or T-175 flasks to 85–90% confluency.
2) On the day of experiment, aspirate growth media, and rinse cells with PBS.
3) Remove PBS, and add 1 to 2 mL 0.02% EDTA solution to detach cells (Sigma, P/N 8008). To facilitate detachment of cells, incubate for 3 to 5 minutes at 37° C.
4) Resuspend cells by adding 10 mL growth media to cell suspension. Count cells, and then centrifuge the cells at 1000–1500×g for 5 minutes to form a pellet.
5) Wash cell pellet once with KRBG.
6) Resuspend cells in Stimulation Buffer to desired density (e.g., 1×10$^6$ cells/mL will give 5,000 cells/well if 5 μL/well are dispensed in a 384-well plate). Incubate for 10 minutes at room temperature.
    Stimulation Buffer (containing 0.75 mM IBMX in KRBG Buffer; make fresh on day of experiment).
    10 mL KRBG Buffer (pH 7.4)
    9.4 μL 800 mM IBMX
7) Dispense 5 μL cell suspension to wells in a 384-well plate.
8) Add 10 μL 1.5×forskolin or PBS to the cells in suspension. Gently mix, and incubate at 37° C. for 15 minutes.
    Forskolin, 1.5×(20 μM final concentration)
    3000 μL PBS (pH 7.4) containing
    3.0 μL of 30 mM forskolin (30 μM stock)
9) Add 5 μL 4×Ly×Buffer to the cells, and incubate for 10 minutes to terminate the stimulation and to lyse the cells. To facilitate cell lysis, place plate on a plate shaker for 10 minutes after adding the lysis reagent.
10) Add 10 μL Antibody followed by 10 μL Tracer for HEFP detection directly in the wells, and incubate as desired (e.g., as indicated in Example 3). Be sure to include any necessary controls and/or calibration curve.

Example 9

This example shows an assay for cAMP and selected modulators of receptors and enzymes that generate cAMP in whole cells. Specifically, FIG. 13 shows the effects of various modulators on cAMP levels in cultured T47D cells, measured using the reagents and methods of Examples 3 and 8. Here, T47D cells were washed and treated according to the protocol in Example 8. The cells were incubated for a predetermined period, and then lysed. Polarization reagents were added, and the sample was examined using an ANALYST™ light-detection platform (LJL BioSystems, Inc.) according to relevant portions of the protocol in Example 3. The results show that the assay responds as expected to agents that modulate cAMP production. In particular, cAMP production was stimulated by forskolin and isoproterenol, and inhibited by propranolol. Forskolin is a known nonspecific stimulator of adenylyl cyclase. Isoproterenol is a beta-adrenergic agonist that stimulates cAMP production by the receptor's normal specific coupling to adenylyl cyclase.

Example 10

This example shows assays for hormones whose cellular responses are mediated by cAMP. Specifically, the assays described here for cAMP may be used to measure the presence and/or activity of the following hormones, among others.

| Selected Hormone-induced Cellular Responses Mediated by cAMP | | |
|---|---|---|
| Target Tissue | Hormone | Major Response |
| Thyroid gland | Thyroid-stimulating hormone (TSH) | Thyroid hormone synthesis and secretion |
| Adrenal cortex | Adrenocorticotropic hormone (ACTH) | Cortisol secretion |
| Ovary | Luteinizing hormone (LH) | Progesterone secretion |
| Muscle | Adrenaline | Glycogen breakdown |
| Bone | Parathormone | Bone resorption |
| Heart | Adrenaline | Increase in heart rate and force of contraction |
| Liver | Glucagon | Glycogen breakdown |
| Kidney | Vasopressin | Water resorption |
| Fat | Adrenaline, ACTH, glucagon, TSH | Triglyceride breakdown |

Example 11

This example shows a direct assay for cell-signaling receptors. Specifically, a labeled ligand may be selected that binds specifically to an activated form of a receptor. The labeled ligand, then, will exhibit a shift in luminescence polarization when bound to the activated receptor. The assay also can be constructed to assess the concentration of activated receptor in a sample. This can be done in the context of membrane or tissue samples or in a cellular suspension. An increase in the polarization of emitted luminescence will be correlated with the concentration of activated receptor in the sample.

An example of such a labeled ligand is a nonhydrolyzable (stabilized) analog of GTP, such as F1-GTP(γ-S), where F1 denotes a luminophore. GTP and other specific guanine nucleotide forms bind to the activated forms of a class of receptors variously known as G-protein-coupled receptors, serpentine receptors, seven-pass transmembrane receptors, and 7 transmembrane-spanning domain receptors. The GTP (γ-S) (or other nonhydrolyzable form) is labeled with the luminophore (such as fluorescein) such that the GTP(γ-S) still retains activated-receptor-binding properties. Activation of the relevant receptor, such as the thrombin receptor or the various opioid receptors, can then be measured in an appropriately designed assay, for example, by measuring the increase in polarization associated with binding. A nonhydrolyzable GTP analog will tend to remain bound to the receptor longer than GTP itself, facilitating measurement of the binding.

As described above, the nonpeptide tracer moiety also may be a product of the activation of a receptor, such as cAMP or cGMP. Labeled forms of these secondary messengers are useful in assays to determine signaling levels by establishing competing binding for an antibody or other specific binding pair member between the labeled tracer and the cAMP or cGMP generated from the receptor activation.

These assays also can be used to determine the ability of candidate drugs to affect the level of activation of a receptor. The luminescence polarization assay is performed in the presence and the absence of the candidate drug. Drugs that interfere with the activation of the receptor will diminish the level of enhanced polarization.

Example 12

This example shows a general assay for activation of GTP-binding proteins. Specifically, the labeled ligand of Example 11 may be used to assay for the activation of any GTP-binding protein, based on the decrease in polarization that will accompany binding of the luminescent analog of GTP to the GTP-binding proteins during activation. Suitable GTP-binding proteins include the trimeric G-proteins and the Ras superfamily of monomeric GTPases, among others.

Example 13

This example shows assays for trimeric G-proteins. Specifically, the assays of Examples 11 and 12 may be used to measure the presence and/or activity of the following G-proteins, among others.

Major Families of Trimeric G-Proteins

| Family | Selected Examples | α Sub-units | Functions | Effects of Selected Bacterial Toxins |
|---|---|---|---|---|
| I | $G_s$ | $α_s$ | Activates adenylyl cyclase Activates $Ca^{2+}$ channels | Cholera activates |
| | $G_{olf}$ | $α_{olf}$ | Activates adenylyl cyclase in olfactory sensory neurons | Cholera activates |
| II | Gi | $α_i$ | Inhibits adenylyl cyclase Activates $K^+$ channels | Pertussis inhibits |
| | $G_o$ | $α_o$ | Activates $K^+$ channels Inactivates $Ca^{2+}$ channels Activates phospholipase C-β | Pertussis inhibits |
| | $G_{t(transducin)}$ | $α_t$ | Activates cGMP phosphodiesterase in vertebrate rod photoreceptors | Cholera activates Pertussis inhibits |
| III | $G_q$ | $α_q$ | Activates phospholipase C-β | No effect |

Example 14

This example shows assays for components of the inositol-phospholipid signaling pathway, including associated G-proteins. Generally, the assays include luminescence polarization assays directed to intermediates of this pathway, such as 1,4,5 IP3. The assays include a tracer form of the intermediate and a specific binding partner of the intermediate and tracer. The tracer may include a luminophore attached by a suitable chemistry to the intermediate (such as a fluorescein succinyl-labeled IP3). The binding partner may include an antibody that specifically binds to the intermediate and tracer. Assays may be performed as shown in FIG. 5, with the intermediate taking the place of the cyclic nucleotide. Assays for associated G-proteins may be performed as shown in FIG. 6. These assays may be used to measure the presence, concentration, and/or activity of intermediates, enzymes, and/or receptors involved, in this pathway, or they may be directed to associated tissues and responses, as indicated in the following table:

Selected Hormone-induced Cellular Responses Mediated by G-Protein-linked Receptors Coupled to the Inositol-Phospholipid Signal Pathway

| Target Tissue | Signaling Molecule | Major Response |
|---|---|---|
| Liver | Vasopressin | Glycogen breakdown |
| Pancreas | Acetylcholine | Amylase secretion |
| Smooth muscle | Acetylcholine | Contraction |
| Mast cells | Antigen | Histamine secretion |
| Blood platelets | Thrombin | Aggregation |

Example 15

This example shows assays for integrated cell signaling mechanisms. Specifically, the assays described here for cyclic nucleotides and GTP-binding proteins may be performed together and/or performed in combination with the kinase assays described in the PCT Patent Application Serial No. PCT/US00/16025, filed Jun. 9, 2000, which is incorporated herein by reference. Such combination assays permit study of signaling mechanisms involving multiple pathways.

Example 16

This example shows assays with improved signals, signal-to-noise ratios, and/or signal-to-background ratios.

Signal may be enhanced in several ways, including (1) using a high color temperature light source, such as a xenon arc lamp, in a continuous illumination mode, (2) using a dichroic or multi-dichroic beamsplitter, and/or (3) using a sample holder whose shape is "matched" to the shape of the optical beam of the instrument, especially if the sample holder is elevated to bring the sample closer to a detector. The high color temperature light source increases the number of usable photons, which is important because the lower limit of the signal-to-noise ratio is set by the square root of the total number of photons collected in the measurement. These enhancements are described in more detail in the following U.S. Patent Applications, which are incorporated herein by reference: Ser. Nos. 09/349,733, 09/478,819, and 09/494,407.

Signal-to-noise ratios can be enhanced at least in part by increasing signals, for example, by using the techniques described in the previous paragraph.

Signal-to-background ratios can be enhanced in several ways, including (1) using confocal optical systems having a sensed volume to avoid luminescence from the microplate walls, (2) selecting a microplate or other substrate that increases the signal and reduces the luminescent background from materials in the microplate, (3) selecting the light sources, luminescence filters, optics, signal collection electronics, and mechanical system used in the luminescence detection optical system for maximum signal-to-background ratio, and (4) utilizing signal processing, background subtraction, and luminescence lifetime techniques, particularly FLAMe™ methodology for background reduction, as described below. These enhancements are described in more detail in the following U.S. Patent and U.S. Patent Applications, which are incorporated herein by reference: U.S. Pat. Nos. 6,071,748, 09/349,733, 09/478,819, and 09/494,407.

Example 17

This example shows mechanisms for increasing the change in polarization that accompanies a change in binding, so that the change in binding can be measured more easily. These mechanisms may be used in any of the assays described here involving luminescently labeled species, such as labeled cyclic nucleotides and labeled nonhydrolyzable GTP analogs, among others.

The change in polarization upon binding can be increased by making any linker between the luminophore and the labeled species (e.g., the cyclic nucleotide or GTP analog) as short and/or rigid as possible, while maintaining relevant substrate properties for the enzymes involved in the assay. Short and/or rigid linkers will restrict luminophore motion relative to the labeled species, reducing the "propeller effect" so that the luminophore more accurately reports the motion of both the free and bound labeled species. The rigidity of the linker may be increased by avoiding using hexanoic acid linkers, which typically are long and flexible, and by using cyclic linkers and amide groups in place of methylene groups, among other mechanisms.

The change in polarization upon binding also can be increased by including an appropriately positioned energy transfer acceptor on the binding partner, so that energy transfer will occur from the luminophore to the acceptor upon incorporation. Such energy transfer will shorten the lifetime of the luminophore, thereby increasing its polarization (because polarization varies inversely with lifetime, all else being equal).

The change in polarization upon binding also can be increased by decreasing the mobility of the binding partner for the labeled species. Mobility can be decreased by increasing the size of the binding partner, either directly or by forming a complex with a mass label. Suitable mass labels include other molecules and beads, among others. The use of mass labels is described in detail in PCT Patent Application Serial No. PCT/US99/24707, which is incorporated herein by reference. Mobility also can be decreased by attaching the binding partner to a surface, such as the surface of a sample holder. Attachment to other molecules, beads, and/or surfaces may be accomplished using any of a number of well-known reactive groups.

Example 18

This example describes principles of luminescence polarization assays. Here, luminescence refers to the absorption and subsequent re-emission of light by a luminescent molecule, or "luminophore," and polarization refers to the direction of the light's electric field, which generally is perpendicular to the direction of the light's propagation. In a luminescence polarization assay, specific molecules within a composition are labeled with one or more luminophores. The composition then is illuminated with polarized excitation light, which preferentially excites luminophores having absorption dipoles aligned parallel to the polarization of the excitation light. These molecules subsequently decay by preferentially emitting light polarized parallel to their emission dipoles. The extent of polarization of the total emitted light depends on the extent of molecular reorientation during the time interval between luminescence excitation and emission, which is termed the luminescence lifetime, $\tau$. In turn, the extent of molecular reorientation depends on the luminescence lifetime and the size, shape, and environment of the reorienting molecule. Thus, luminescence polarization assays may be used to quantify binding reactions and enzymatic activity, among other applications. In particular, molecules commonly rotate (or "tumble") via diffusion, with a rotational correlation time $\tau_{rot}$ that is proportional to their volume, or the cube of their radius of gyration. (This cubic dependence on radius makes polarization assays very sensitive to binding.) Thus, during their luminescence lifetime, relatively large molecules will not reorient significantly, so that their total luminescence will be relatively polarized. In contrast, during the same time interval, relatively small molecules will reorient significantly, so that their total luminescence will be relatively unpolarized.

The relationship between polarization and intensity is expressed by the following equation:

$$P = \frac{I_\| - I_\perp}{I_\| + I_\perp} \qquad (2)$$

Here, P is the polarization, $I_\|$ is the intensity of luminescence polarized parallel to the polarization of the excitation light, and $I_\perp$ is the intensity of luminescence polarized perpendicular to the polarization of the excitation light. P generally varies from zero to one-half for randomly oriented molecules (and zero and one for aligned molecules). If there is little rotation between excitation and emission, $I_\|$ will be relatively large, $I_\perp$ will be relatively small, and P will be close to one-half. (P may be less than one-half even if there is no rotation; for example, P will be less than one-half if the absorption and emission dipoles are not parallel.) In contrast, if there is significant rotation between absorption and emission, $I_\|$ will be comparable to $I_\perp$, and P will be close to zero. Polarization often is reported in milli-P units (1000× P), which for randomly oriented molecules will range between 0 and 500, because P will range between zero and one-half.

Polarization also may be described using other equivalent quantities, such as anisotropy. The relationship between anisotropy and intensity is expressed by the following equation:

$$r = \frac{I_\| - I_\perp}{I_\| + 2I_\perp} \quad (3)$$

Here, r is the anisotropy. Polarization and anisotropy include the same information, although anisotropy may be more simply expressed for systems containing more than one luminophore. In the description and claims that follow, these terms may be used interchangeably, and a generic reference to one should be understood to imply a generic reference to the other.

The relationship between polarization and rotation is expressed by the Perrin equation:

$$\left(\frac{1}{P} - \frac{1}{3}\right) = \left(\frac{1}{P_0} - \frac{1}{3}\right) \cdot \left(1 + \frac{\tau}{\tau_{rot}}\right) \quad (4)$$

Here, $P_0$ is the polarization in the absence of molecular motion (intrinsic polarization), $\tau$ is the luminescence lifetime (inverse decay rate) as described above, and $\tau_{rot}$ is the rotational correlation time (inverse rotational rate) as described above.

The Perrin equation shows that luminescence polarization assays are most sensitive when the luminescence lifetime and the rotational correlation time are similar. Rotational correlation time is proportional to molecular weight, increasing by about 1 nanosecond for each 2,400 dalton increase in molecular weight (for a spherical molecule). For shorter lifetime luminophores, such as fluorescein, which has a luminescence lifetime of roughly 4 nanoseconds, luminescence polarization assays are most sensitive for molecular weights less than about 40,000 daltons. For longer lifetime probes, such as Ru(bpy)$_2$dcbpy (ruthenium 2,2'-dibipyridyl 4,4'-dicarboxyl-2,2'-bipyridine), which has a lifetime of roughly 400 nanoseconds, luminescence polarization assays are most sensitive for molecular weights between about 70,000 daltons and 4,000,000 daltons.

Luminescence polarization assays may be used in a variety of formats. In one format, the concentration of an analyte in solution can be measured by supplying a labeled tracer that competes with the analyte for a binding moiety, particularly a binding moiety larger than the labeled tracer. In this "competitive" format, the concentration of the analyte is inversely correlated with the enhancement of luminescence polarization in the light emitted by the tracer when it competitively binds the common moiety. In another format, the concentration of a target can be measured by supplying a labeled tracer that is capable of binding the target. In this case, the enhancement of polarization is a direct measure of the concentration of target. The target further may be, for example, an activated receptor, where activation can be indirectly measured by the directly measured concentration of a generated molecule or by its binding to labeled tracer per se.

Although the invention has been disclosed in its preferred forms, the specific embodiments thereof as disclosed and illustrated herein are not to be considered in a limiting sense, because numerous variations are possible. As used herein, singular terms do not preclude the use of more than one of the associated element, and embodiments using more than one of a particular element are within the spirit and scope of the invention. Applicants regard the subject matter of their invention to include all novel and nonobvious combinations and subcombinations of the various elements, features, functions, and/or properties disclosed herein. No single feature, function, element or property of the disclosed embodiments is essential. The following claims define certain combinations and subcombinations of features, functions, elements, and/or properties that are regarded as novel and nonobvious. Other combinations and subcombinations may be claimed through amendment of the present claims or presentation of new claims in this or a related application. Such claims, whether they are broader, narrower, equal, or different in scope to the original claims, also are regarded as included within the subject matter of applicants' invention.

We claim:

1. A method of identifying a compound as a modulator of G-protein-linked receptor activity that generates or consumes a cyclic nucleotide through the action of a cyclase or phosphodiesterase, comprising:

conducting a G-protein-linked-receptor mediated reaction that generates or consumes a cyclic nucleotide in the presence of a candidate compound;

contacting, in vitro, a product of the reaction with a luminescent tracer and with the opposite member of a specific binding pair to the cyclic nucleotide, wherein the tracer and the cyclic nucleotide compete for binding to the opposite member of the specific binding pair;

illuminating the tracer with polarized light, wherein the light is capable of inducing emission of polarized light from the tracer;

detecting the extent of polarization of light emitted from the tracer; and identifying the candidate compound as a modulator of the reaction based on the extent of polarization of the emitted light.

2. The method of claim 1, wherein the cyclic nucleotide is selected from the group consisting of cAMP and cGMP.

3. The method of claim 1, wherein the opposite member of a specific binding pair is an immunological binding partner.

4. The method of claim 1, wherein the extent of polarization is determined using a function selected from the group consisting of polarization and anisotropy.

5. The method of claim 1, wherein the extent of polarization of the emitted light is inversely correlated with the concentration of the cyclic nucleotide.

6. The method of claim 1, further comprising determining the concentration of the cyclic nucleotide.

7. The method of claim 1, wherein the reaction is conducted using whole cells.

8. The method of claim 1, wherein the reaction is conducted using lysed cells.

9. The method of claim 1, wherein the reaction generates a cyclic nucleotide.

10. The method of claim 9, wherein the reaction generates a cyclic nucleotide through the action of a cyclase.

11. The method of claim 1, wherein the reaction consumes a cyclic nucleotide.

12. The method of claim 11, wherein the reaction consumes a cyclic nucleotide through the action of a phosphodiesterase.

13. The method of claim 1, further comprising repeating the steps of conducting, contacting, illuminating, and detecting in the absence of a candidate compound, wherein the step of identifying the candidate compound as a modulator includes comparing the extent of polarization of the emitted light based on the reaction conducted in the presence of the candidate compound to the extent of polarization of the emitted light based on the reaction conducted in the absence of the candidate compound.

14. The method of claim 13, the reaction generating a cyclic nucleotide, wherein an increase in the extent of polarization when the reaction is conducted in the presence of the candidate compound in comparison with the extent of polarization when the reaction is conducted in the absence of the candidate compound identifies the candidate compound as an inhibitor of the reaction, and wherein a decrease in the extent of polarization when the reaction is conducted in the presence of the candidate compound in comparison with the extent of polarization when the reaction is conducted in the absence of the candidate compound identifies the candidate compound as an agonist of the reaction.

15. The method of claim 13, the reaction consuming a cyclic nucleotide, wherein an increase in the extent of polarization when the reaction is conducted in the presence of the candidate compound in comparison with the extent of polarization when the reaction is conducted in the absence of the candidate compound identifies the candidate compound as an agonist of the reaction, and wherein a decrease in the extent of polarization when the reaction is conducted in the presence of the candidate compound in comparison with the extent of polarization when the reaction is conducted in the absence of the candidate compound identifies the candidate compound as an inhibitor of the reaction.

16. The method of claim 1, the reaction generating a cyclic nucleotide, wherein the step of conducting the reaction includes providing a nucleotide triphosphate.

17. The method of claim 1, the reaction consuming a cyclic nucleotide, wherein the step of conducting the reaction includes providing the cyclic nucleotide.

18. The method of claim 1, further comprising repeating the steps of conducting, contacting, illuminating, detecting, and identifying for a different candidate compound.

19. The method of claim 18, at least one of the steps being performed using a microplate, wherein a different well of the microplate is used for each different candidate compound.

20. The method of claim 1, wherein at least one of the steps of conducting, contacting, illuminating, detecting, and identifying is performed using a microplate.

21. The method of claim 1, the step of conducting the reaction being performed in a reaction volume, wherein the step of contacting includes adding the luminescent tracer and the opposite member of a specific binding pair to the reaction volume.

22. The method of claim 1, wherein the luminescent tracer comprises a cyclic nucleotide coupled to a luminophore.

23. The method of claim 1, the step of conducting a reaction being performed inside a cell, further comprising the step of lysing the cell to obtain the product of the reaction prior to the steps of contacting, illuminating, detecting, and identifying.

24. The method of claim 1 wherein the G-protein-linked receptor generates cAMP through G-protein activation and adenylate cyclase activity.

25. The method of claim 1, wherein the candidate compound is a modulator of the G-protein-linked receptor.

* * * * *